US008460746B2

(12) United States Patent
Dadd et al.

(10) Patent No.: US 8,460,746 B2
(45) Date of Patent: Jun. 11, 2013

(54) METHOD OF FORMING INSULATED CONDUCTIVE ELEMENT HAVING A SUBSTANTIALLY CONTINUOUS BARRIER LAYER FORMED VIA RELATIVE MOTION DURING DEPOSITION

(75) Inventors: Fysh Dadd, Lane Cove (AU); Edmond D. Capcelea, Bondi Junction (AU); Peter Schuller, Turramurra (AU); Jane L. Rapsey, Berowra (AU)

(73) Assignee: Cochlear Limited, Macquarie University, NSW (AU)

( * ) Notice: Subject to any disclaimer, the term of this patent is extended or adjusted under 35 U.S.C. 154(b) by 534 days.

(21) Appl. No.: 12/556,326

(22) Filed: Sep. 9, 2009

(65) Prior Publication Data

US 2011/0056725 A1 Mar. 10, 2011

(51) Int. Cl.

| | |
|---|---|
| ***B05D 5/12*** | (2006.01) |
| ***C23C 16/00*** | (2006.01) |
| ***A61L 33/00*** | (2006.01) |

(52) U.S. Cl.

USPC ........... 427/117; 427/2.1; 427/2.31; 427/178; 427/255.5; 427/255.6; 427/295

(58) Field of Classification Search

USPC ................... 427/117, 178, 255.5, 255.6, 295, 427/2.2, 2.31

See application file for complete search history.

(56) References Cited

U.S. PATENT DOCUMENTS

| | | | | |
|---|---|---|---|---|
| 2,665,229 | A | | 1/1954 | Schuler et al. |
| 3,342,754 | A | | 9/1967 | Gorham |
| 3,511,212 | A | | 5/1970 | Burns |
| 4,220,117 | A | | 9/1980 | Shinohara |
| 4,654,880 | A | | 3/1987 | Sontag |
| 4,741,339 | A | | 5/1988 | Harrison et al. |
| 4,841,908 | A | | 6/1989 | Jacobson et al. |
| 5,121,706 | A | | 6/1992 | Nichols et al. |
| 5,201,903 | A | | 4/1993 | Corbett, III et al. |
| 5,439,736 | A | * | 8/1995 | Nomura ..................... 428/308.4 |
| 5,914,701 | A | | 6/1999 | Gersheneld et al. |
| 5,972,160 | A | | 10/1999 | Straemke |
| 6,045,877 | A | | 4/2000 | Gleason et al. |
| 6,115,636 | A | | 9/2000 | Ryan |
| 6,223,018 | B1 | | 4/2001 | Fukumoto et al. |
| 6,306,176 | B1 | | 10/2001 | Whitbourne |

(Continued)

FOREIGN PATENT DOCUMENTS

| | | | |
|---|---|---|---|
| AU | 2002218936 | C1 | 9/2002 |
| AU | 2005201357 | A1 | 10/2005 |

(Continued)

OTHER PUBLICATIONS

International Application No. PCT/IB2010/054079, International Preliminary Report on Patentability mailed on Mar. 22, 2012, 5 Pages.

*Primary Examiner* — Brian K Talbot

(74) *Attorney, Agent, or Firm* — Kilpatrick, Townsend & Stockton, LLP.

(57) ABSTRACT

Coating an elongate, uncoated conductive element with a substantially continuous barrier layer. An uncoated conductive element is around a frame comprising spaced supports. During deposition, the relative position of the conductive element to the frame is adjusted so that all sections of the conductive element are physically separated from the supports for a time that is sufficient to form a desired coating of barrier material on all sections of the conductive element.

34 Claims, 38 Drawing Sheets

U.S. PATENT DOCUMENTS

| | | | | |
|---|---|---|---|---|
| 6,421,569 | B1 | 7/2002 | Treaba et al. | |
| 6,574,510 | B2 | 6/2003 | Von Arx et al. | |
| 6,748,094 | B1 | 6/2004 | Tziviskos et al. | |
| 6,766,201 | B2 | 7/2004 | Von Arx et al. | |
| 6,849,295 | B2 | 2/2005 | Hundt | |
| 6,924,773 | B1 | 8/2005 | Paratte | |
| 7,020,298 | B1 | 3/2006 | Tziviskos et al. | |
| 7,088,267 | B2 | 8/2006 | Tajima | |
| 7,171,177 | B2 | 1/2007 | Park et al. | |
| 7,181,024 | B1 | 2/2007 | Oba et al. | |
| 7,206,423 | B1 | 4/2007 | Feng et al. | |
| 7,392,091 | B2 | 6/2008 | Bruinsma | |
| 7,406,105 | B2 | 7/2008 | DelMain et al. | |
| 8,301,261 | B2 | 10/2012 | Bruinsma | |
| 2003/0099858 | A1 | 5/2003 | Duggal et al. | |
| 2004/0138723 | A1 | 7/2004 | Malick et al. | |
| 2004/0202339 | A1 | 10/2004 | O'Brien, Jr. et al. | |
| 2007/0127745 | A1 * | 6/2007 | Gibson et al. | 381/151 |
| 2007/0128940 | A1 | 6/2007 | Ho et al. | |
| 2007/0256928 | A1 | 11/2007 | Sutton et al. | |
| 2007/0261638 | A1 | 11/2007 | Awata et al. | |
| 2009/0030488 | A1 | 1/2009 | Bruinsma | |
| 2009/0124201 | A1 | 5/2009 | Meskens | |
| 2009/0165921 | A1 | 7/2009 | Kaiser | |
| 2009/0194505 | A1 | 8/2009 | Slafer | |
| 2009/0280153 | A1 * | 11/2009 | Hunter et al. | 424/423 |
| 2011/0056726 | A1 | 3/2011 | Schuller et al. | |
| 2011/0060396 | A1 | 3/2011 | Schuller et al. | |
| 2011/0151111 | A1 | 6/2011 | Lawrence et al. | |

FOREIGN PATENT DOCUMENTS

| | | | |
|---|---|---|---|
| CN | 102597298 | A | 7/2012 |
| JP | 06-136538 | A | 5/1994 |
| WO | 0071063 | A1 | 11/2000 |
| WO | 2007/126343 | A1 | 11/2007 |
| WO | 2011/030305 | A2 | 3/2011 |
| WO | 2011/030305 | A3 | 8/2011 |

* cited by examiner

2200B

METHOD OF FORMING INSULATED CONDUCTIVE ELEMENT HAVING A SUBSTANTIALLY CONTINUOUS BARRIER LAYER FORMED VIA RELATIVE MOTION DURING DEPOSITION

CROSS-REFERENCE TO RELATED APPLICATIONS

The present application is related to commonly owned and co-pending U.S. Utility patent applications entitled "An Insulated Conductive Element Comprising Substantially Continuously Coated Sections Separated By Uncoated Gaps," filed Sep. 9, 2009; "An Insulated Conductive Element Comprising Substantially Continuous Barrier Layer Formed Through Multiple Coatings," filed Sep. 9, 2009; and "An Insulated Conductive Element Having A Substantially Continuous Barrier Layer Formed Through Continuous Vapor Deposition," filed Sep. 9, 2009. The content of these applications is hereby incorporated by reference herein.

BACKGROUND

1. Field of the Invention

The present invention relates generally to coated conductive elements, and more particularly, to an insulated conductive element having a substantially continuous barrier layer formed via relative motion during deposition.

2. Related Art

The use of medical devices to provide therapy to individuals for various medical conditions has become more widespread as the therapeutic benefits of such devices become more widely appreciated and accepted throughout the population. For example, hearing aids, implantable pacemakers, defibrillators, functional electrical stimulation devices, prosthetic hearing devices, organ assist and replacement devices, sensors, drug delivery devices and other medical devices, have successfully performed life saving, lifestyle enhancement or other therapeutic functions for many individuals. One common usage of medical devices is to treat an individual's hearing loss.

Hearing loss, which may be due to many different causes, is generally of two types, conductive and sensorineural. In some cases, a person suffers from both types of hearing loss. Conductive hearing loss occurs when the normal mechanical pathways for sound to reach the cochlea are impeded, for example, by damage to the ossicles. Individuals suffering from conductive hearing loss typically have some form of residual hearing because the hair cells in the cochlea are undamaged. As a result, individuals suffering from conductive hearing loss typically receive a hearing prosthesis that generates mechanical motion of the cochlea fluid.

In many people who are profoundly deaf, however, the reason for their deafness is sensorineural hearing loss. Sensorineural hearing loss occurs when there is damage to the inner ear, or to the nerve pathways from the inner ear to the brain. As such, many individuals suffering from sensorineural hearing loss are thus unable to derive suitable benefit from hearing prostheses that generate mechanical motion of the cochlea fluid. As a result, hearing prostheses that deliver electrical stimulation to nerve cells of the recipient's auditory system have been developed. Such electrically-stimulating hearing prostheses deliver electrical stimulation to nerve cells of the recipient's auditory system thereby providing the recipient with a hearing percept. Electrically-stimulating hearing prostheses include, for example, auditory brain stimulators and cochlear prostheses (commonly referred to as cochlear prosthetic devices, cochlear implants, cochlear devices, and the like; simply "cochlear implants" herein.)

Oftentimes sensorineural hearing loss is due to the absence or destruction of the cochlear hair cells which transduce acoustic signals into nerve impulses. Cochlear implants provide a recipient with a hearing percept by delivering electrical stimulation signals directly to the auditory nerve cells, thereby bypassing absent or defective hair cells that normally transduce acoustic vibrations into neural activity. Such devices generally use a stimulating assembly implanted in the cochlea so that the electrodes may differentially activate auditory neurons that normally encode differential pitches of sound. As is known in the art, a stimulating assembly comprises a plurality of electrode contacts each individually electrically connected to a stimulator unit via elongate conductive elements, such as wires. In practice, a coating is applied to the surface of the conductive elements for one or more of electrical and physical insulation, passivation, biocompatibility and immobilization of microscopic particles.

SUMMARY

In one aspect of the present invention, a method of coating an elongate, uncoated conductive element with a substantially continuous barrier layer is provided. The method comprises: positioning the uncoated conductive element around a frame comprising spaced supports such that sections of the conductive element are positioned in contact with the two or more supports; depositing a barrier material on the conductive element to form the barrier layer; adjusting the relative position of the conductive element to the frame during deposition such that the sections of the conductive element are physically separated from the supports for a time that is sufficient to form the barrier substantially continuous barrier layer on the conductive element; and removing the coated conductive element from the frame.

In another aspect of the present invention, a method of coating an elongate, uncoated conductive element is provided. The method comprises: positioning the uncoated conductive element around a frame comprising spaced supports such that sections of the conductive element are positioned in contact with two or more supports; depositing a barrier material on the conductive element; moving at least one of the conductive element and the frame relative to one another during deposition of the barrier material such that a substantially continuous barrier layer is formed on the surface of the conductive element; and removing the coated conductive element from the frame.

BRIEF DESCRIPTION OF THE DRAWINGS

Embodiments of the present invention are described below with reference to the attached drawings, in which.

DETAILED DESCRIPTION

Conventionally, vapor deposition commonly refers to a process in which a material in a vapor state is condensed to form a solid material. Vapor deposition, which is generally divided into two broad categories known as physical vapor deposition (PVD) and chemical vapor deposition (CVD), is often used to form coatings on objects. Such coatings are provided to, for example, alter the mechanical, electrical, thermal, optical, corrosion resistance, and/or wear properties of the objects.

As described in detail below, embodiments of the present invention are generally directed to using vapor deposition to coat elongate conductive elements with a protective barrier layer. The barrier layer may be applied to the conductive elements for a variety of reasons including providing electrical insulation, biocompatibility, immobilization of microscopic particles, and ensuring that the conductive elements are passive, as well as providing physical isolation of the conductive elements from moisture, chemicals, and other substances. As used herein, a conductive element having a barrier layer in accordance with embodiments of the present invention disposed on the surface thereof is referred to as an insulated conductive element.

In certain embodiments, the barrier layer is a polymeric material. In one particular embodiment, the barrier layer is parylene. Parylene is the generic name for a variety of vapor deposited poly-para-xylylenes. These materials form highly-crystalline polymers that may be applied as conformal coatings and films. Parylene, unlike other polymeric materials, is not manufactured or sold as a polymer. Rather it is produced by vapor-phase deposition and polymerization of para-xylylene or its derivatives.

There are a variety of derivatives and isomers of parylene. The most common variants include Parylene C, Parylene N, and Parylene D. It would be appreciated that other variants of parylene are also commercially available.

Figure 1:
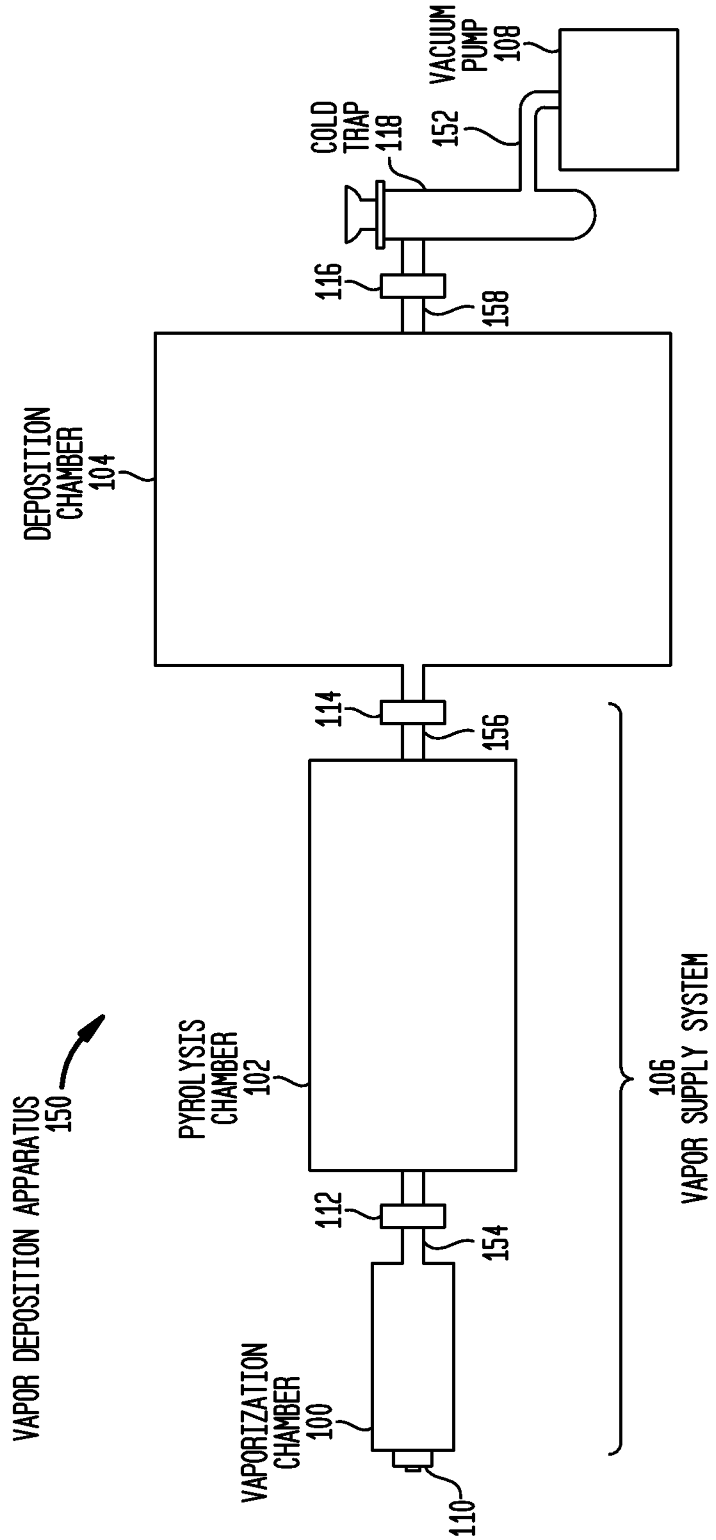
FIG. 1 (PRIOR ART)
FIG. 1 is a simplified schematic view of a conventional vapor deposition apparatus.

FIG. 1 is a simplified schematic diagram of a conventional vapor deposition apparatus 150. Vapor deposition apparatus 150 comprises a vapor supply system 106 configured to supply the necessary vapor material to a deposition chamber 104. In the system illustrated in FIG. 1, vapor supply system 106 includes a vaporization chamber 100 that vaporizes a quantity of a dimer inserted therein via closable aperture 110. As is known in the art, a dimer is a chemical or biological substance consisting of a plurality of bonded monomers.

Vapor supply system 106 further comprises a pyrolysis chamber 102 connected to vaporization chamber 100 by supply line 154. Line 154 includes a valve 112 that controls the flow of vaporized dimer from vaporization chamber 100 to pyrolysis chamber 102. Once transferred to pyrolysis chamber 102, the vaporized dimer is pyrolized at temperatures of approximately 400 to 750 degrees Celsius to form a desired monomer vapor. The monomer vapor is transferred from pyrolysis chamber 102 via supply line 156 into deposition chamber 104. Supply line 156 also includes a control valve 114 that controls the flow of the vapor into deposition chamber 104.

Following deposition and condensation, residual vapor is removed from deposition chamber 104 via exit line 158. Exit line 158 is connected to a cold trap 118 that serves to rapidly condense and polymerize any residual vapors. Vacuum pump 108 is connected to cold trap 118 via vacuum line 152 and maintains continual negative pressure within deposition chamber 104 and cold trap 118.

Conventional vapor deposition systems and apparatuses are known in the art. As such, further details of the vapor deposition apparatus 150 will not be provided herein.

Also as known in the art, a vapor deposition apparatus may be used to provide coatings on various different types of objects, such as components of an implantable medical device. As an example, one type of medical device which may advantageously utilize vapor deposition is a cochlear implant. As is known in the art, a cochlear implant comprises a stimulating electrode assembly implantable in a recipient's cochlea. The stimulating electrode assembly comprises a plurality of electrode contacts individually electrically connected to a stimulator unit via elongate conductive elements, such as wires. The wires connecting the electrode contacts to the stimulator unit are electrically insulated so that the wires may be bundled together for implantation without electrical interference.

Figure 2A:
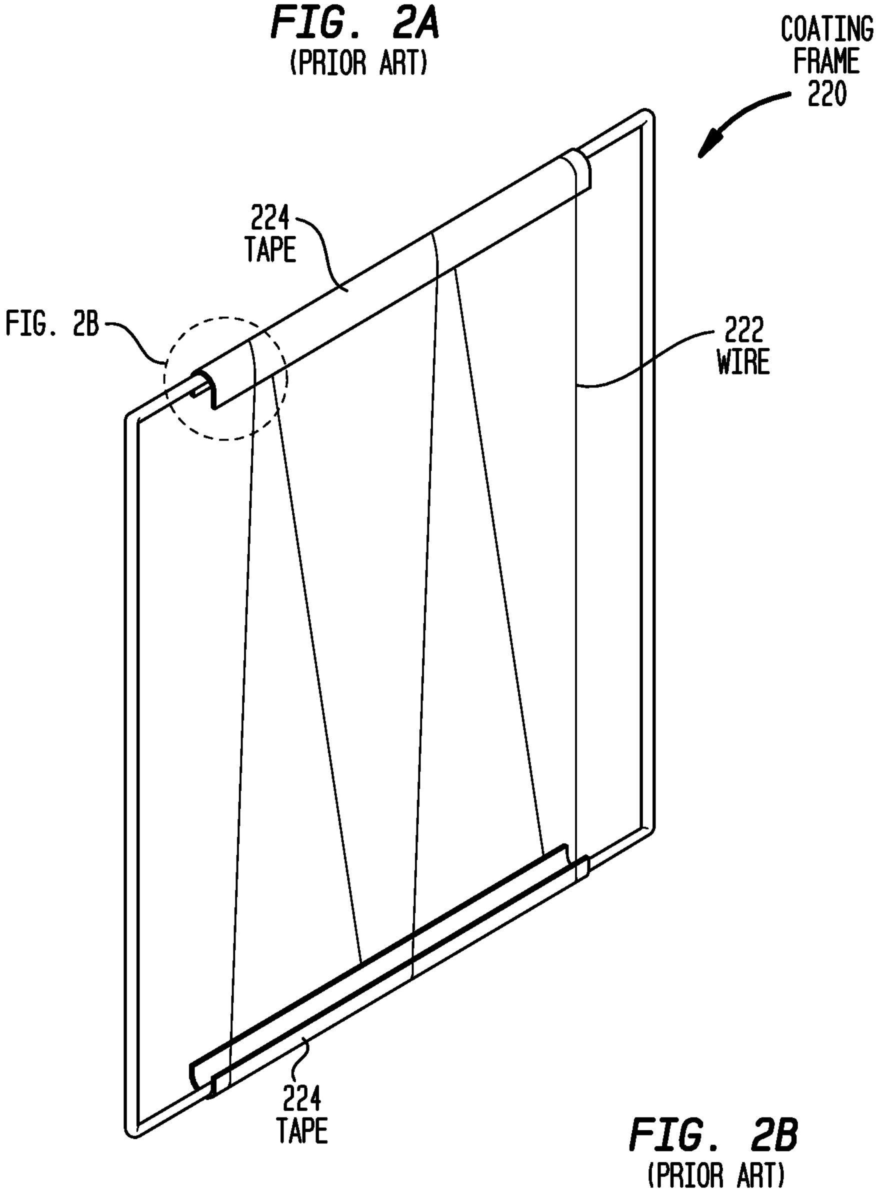
FIG. 2A (PRIOR ART)
FIG. 2A is a perspective view of a conventional coating frame having a wire secured thereto with tape during a conventional chemical deposition process.
Figure 2B:
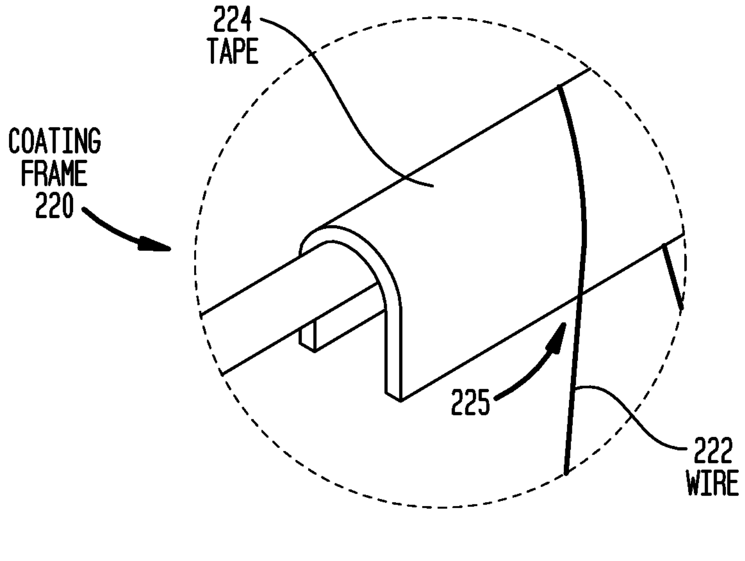
FIG. 2B (PRIOR ART)
FIG. 2B is a cross-sectional, expanded view of a section of the prior art coating frame and wire arrangement of FIG. 2A.
Figure 2C:
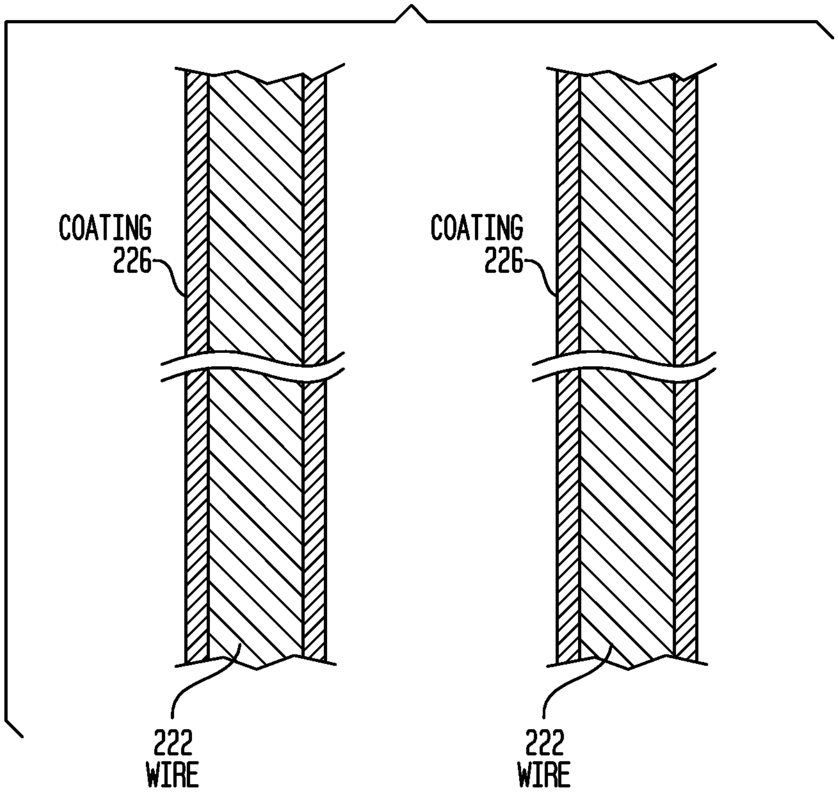
FIG. 2C (PRIOR ART)
FIG. 2C is a cross-sectional side view of two separate prior art coated wires removed from the coating frame of FIGS. 2A and 2B.

In certain circumstances, a vapor deposition process may be used to provide electrically insulated wires for connecting electrodes to a stimulator unit during manufacturing of a cochlear implant. FIGS. 2A-2B illustrate a conventional vapor deposition process for production of coated wires, while FIG. 2C illustrate two separate wires obtained as the result of the conventional process of FIGS. 2A and 2B.

During the conventional wire coating process of FIGS. 2A and 2B, a wire 222 is wound around opposing sides of a rectangular coating frame 220. As shown in FIG. 2A, coating frame 220 comprises four bars or rods that are welded together to form the rectangular shape. Opposing sides of coating frame 220 have double-sided tape 224 secured to the surface thereof.

FIG. 2B is an expanded view of the section of FIG. 2A labeled as FIG. 2B. As shown in FIG. 2B, as wire 222 is wound around coating frame 220, the wire is positioned in contact with an adhesive surface of tape 224. Thus, tape 224 affixes wire 222 to the opposing sides of coating frame 220 thereby preventing any movement of wire 222.

After wire 222 is secured to coating frame 220, the coating frame may be positioned in a deposition chamber, such as deposition chamber 104 of vapor deposition apparatus 150, for deposition of the coating. Following deposition of the coating, coating frame 220 is removed from the deposition chamber and discrete wires are formed from the coated portions of wire 222. More specifically, because wire 222 is secured to coating frame 220 using tape 224, the wire can not be removed from the tape without damaging the wire. Furthermore, because the coating extends across the tape/wire boundary 225, removal of the tape also removes portions of the coating on wire 222, or damages those sections of the wire that are adhered to the tape. Therefore, only those portions of the wire that are not in contact with tape 224 are utilized. This necessitates that discrete, physically separate sections of coated wired 222, shown in FIG. 2C, be cut from the portions of wire 222 extending between the opposing sides of coating frame 220. In certain circumstances, the wound wire 222 is cut at or near each tape/wire boundary 225, and each turn of the wound wire forms two separate coated sections.

As shown in the cross-sectional views of FIG. 2C, the separate sections of coated wire 222 have a conductive core substantially surrounded by a layer of coating 226. Discrete sections of coated wires produced using the above process may be used in the production of conventional cochlear implants and other medical devices.

Figure 3A:
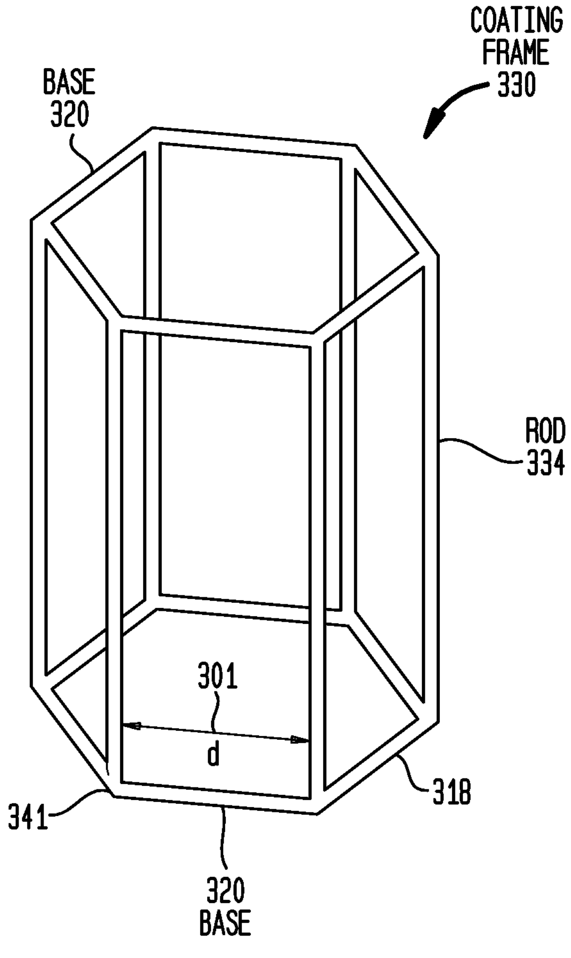
FIG. 3A is a perspective view of a coating frame in accordance with embodiments of the present invention.
Figure 3B:
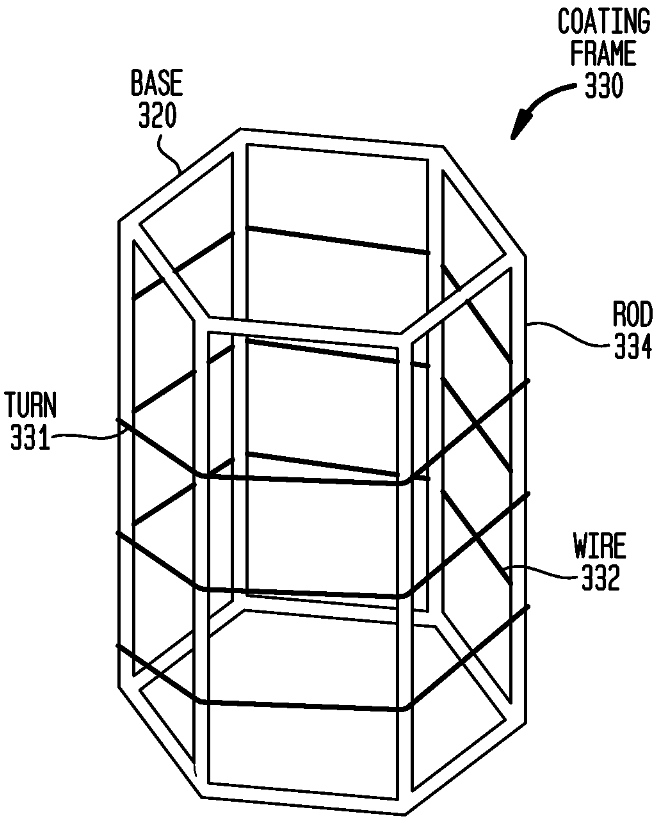
FIG. 3B is a perspective view of the coating frame of FIG. 3A having a wire wound there around, in accordance with embodiments of the present invention.

Embodiments of the present invention are generally directed to producing a contiguous length of a coated conductive element, referred to herein as an insulated conductive element comprising substantially continuously coated sections separated by uncoated gaps. The uncoated gaps are formed at substantially predictable or determinable locations, and have a length that is substantially small relative to the lengths of the coated sections. Certain embodiments of the present invention are directed to using vapor deposition to form the elongate insulated conductive element. FIGS. 3A and 3B illustrate a coating frame 330 that may be used to form such an insulated conductive element. Coating frame 330 may be formed from any material which has sufficient strength to maintain a desired shaped when subjected to the operations described below. In specific embodiments, coating frame 330 is formed from stainless steel.

The elongate conductive elements that may be utilized in embodiments of the present invention include, but are not limited to, single or multi-strand wires, conductive ribbons, shim or carbon nanotube (CNT) yarns, etc. In certain embodiments, the elongate conductive elements have a desired amount of malleability. Furthermore, elongate conductive elements utilized in embodiments of the present invention may have varying lengths. In embodiments of the present invention, the conductive element has a length of approximately 1-100 meters, while in specific embodiments the conductive element has a length of approximately 5-10 meters. It would be appreciated that other lengths may also be utilized. For ease of illustration, embodiments of the present invention will be primarily described herein with reference to a single strand wire 332.

In the embodiments of FIGS. 3A and 3B, coating frame 330 comprises two substantially parallel bases 320, and a plurality of substantially parallel, spaced rods 334 extending between the bases. In the illustrative embodiments of FIGS. 3A and 3B, bases 320 each are hexagonal in shape and comprise six members 318 joined to each other to form vertices 341. Rods 334 extend between opposing vertices 341 of bases 320. Therefore, the distance between adjacent rods 334, illustrated by dimension line 301 in FIG. 3A, is equal to the length of the base member 318 positioned between adjacent vertices 341 to which the adjacent rods 334 are attached.

As shown in FIG. 3B, uncoated wire 332 is wound around rods 334 into a plurality of turns 331. As described in greater detail below, wire 332 is wound under tension such that the wound wire does not move relative to coating frame 330 and remains substantially stationary during subsequent deposition.

Figure 3C:
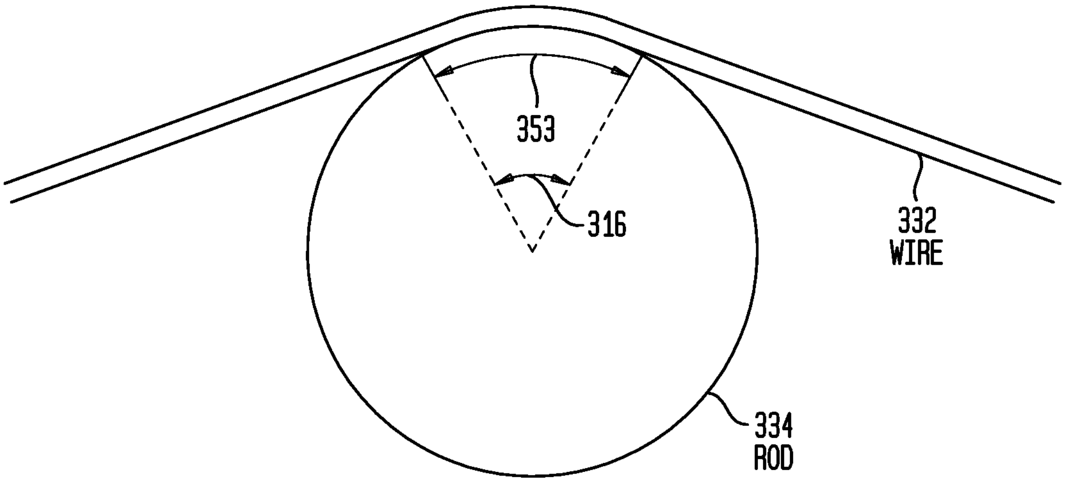
FIG. 3C is a cross-sectional view of a coating frame rod of FIGS. 3A and 3B having a wire in contact therewith in accordance with embodiments of the present invention.

FIG. 3C is a top view of a section of wire 332 positioned in contact with one of the rods 334. As shown, each turn 331 contacts each rod 334 for a length, referred to herein as the wire/rod contact length 353, or simply contact length 353. Because rods 334 have a cylindrical shape, contact length 353 between rod 334 and wire 332 follows an arc defined by angle 316 that corresponds to a portion of the surface of rod 334. As described below, contact length 353 between rod 334 and wire 332 may vary depending on, for example, the shape of rod 334.

It would be appreciated that the contact length between rod 334 and wire 332 may also vary depending on, for example, the number of rods 334 within coating frame 330 that wire is wound around, the distance between rods 334, etc. Regardless of the number of rods 334, etc., the contact length between wire 332 and rods 334 remains substantially small relative to the distance between adjacent rods 334 of coating frame 332.

Figure 3D:
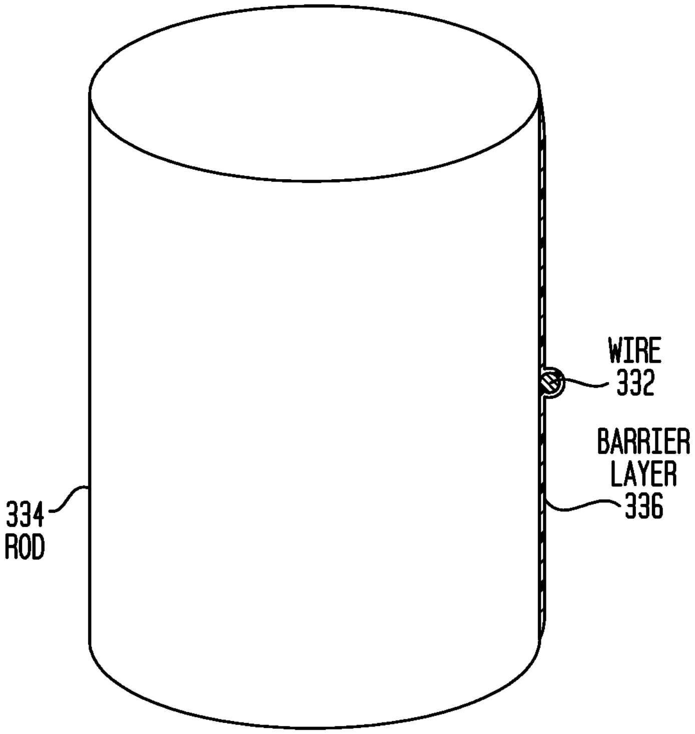
FIG. 3D is a cross-sectional side view of a coated wire prior to removal from the coating frame, in accordance with embodiments of the present invention.

As noted above, after wire 322 is securely wound around coating frame 320 and secured thereto via the wire tension, coating frame 330 is positioned in a deposition chamber, such as deposition chamber 104 of vapor deposition apparatus 150 (FIG. 1), for deposition of a barrier material on wire 332. FIG. 3D is a side view of section of rod 334 and wire 332 illustrated in FIG. 3C. In the embodiments of FIG. 3D, wire 332 and barrier layer 336 are shown in cross-section. For ease of illustration, in the embodiments of FIG. 3D wire 332 and barrier layer 336 are not shown to scale.

It would be appreciated that the thickness of barrier layer 336 may vary. In certain embodiments, wire 332 may have a diameter of approximately 5-100 microns, and barrier layer 336 may have a thickness of approximately 3-10 microns. In specific embodiments, wire may have a diameter of 10-30 microns, and barrier layer 336 may have a thickness of approximately 5-7 microns.

As shown in FIG. 3D, the deposition of the barrier material on wire 332 forms a barrier layer 336 substantially covering the surface of wire 332 that is not in direct contact with rod 334. Because wire 332 is wound under tension, and no additional fixation elements are required, the release of the tension permits the unwinding of wire 332 from coating frame 332 as a unitary, contiguous element, referred to as insulated conductive element 360. A side view of a section of insulated conductive element 360 is shown in FIG. 3E, while a cross-sectional view of insulated conductive element 360 taken along cross-sectional line 3F-3F of FIG. 3E is shown in FIG. 3F.

Figure 3E:
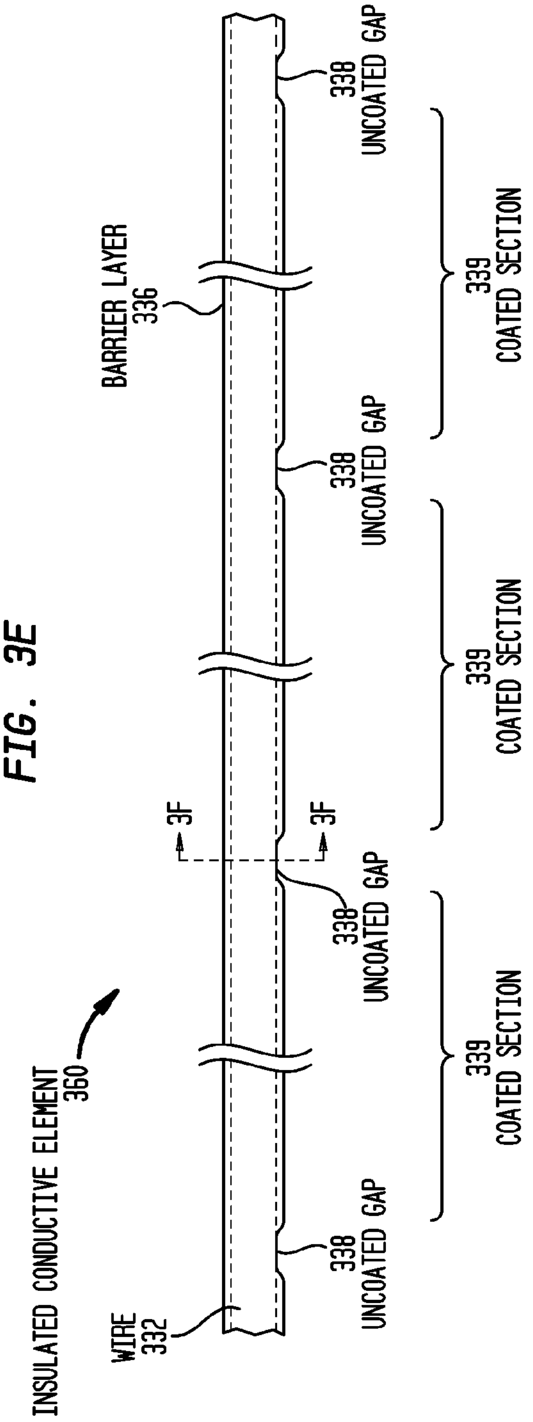
FIG. 3E is a side view of a coated wire following removal of the wire from a coating frame in accordance with embodiments of the present invention.
Figure 3F:
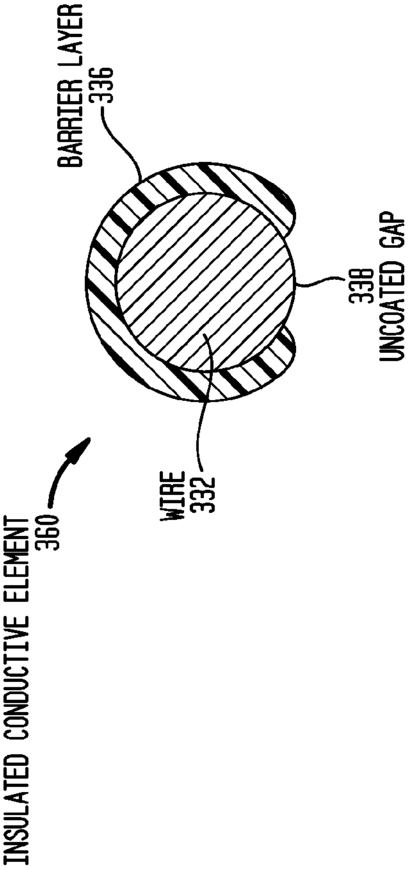
FIG. 3F is a cross-sectional side view of the coated wire of FIG. 3E taken along cross-sectional line 3F-3F.

As shown in FIG. 3E, unwound insulated conductive element 360 comprises a plurality of coated sections 339 separated by uncoated gaps 338. For ease of illustration, portions of each coated section 339 have been omitted from FIG. 3F. The length of coated sections 339 are approximately equal to the distance 301 between adjacent rods 334, while the length of uncoated gaps are approximately equal to the contact length between a rod 334 and wire 332, described above with reference to FIG. 3C. It would be appreciated that these lengths may vary, but the length of uncoated gaps 339 are substantially smaller than the length of coated sections 339.

Also as noted above, the length of coated sections 339 generally correspond to the distance 301 between adjacent rods 334. Therefore, gaps 338 are generally formed at predictable or determinable locations. Because the gaps 338 are formed at predictable or determinable locations, the gaps may be managed during subsequent processing.

It would be appreciated that the embodiments of FIGS. 3A-3F have not been shown to scale. It would also be appreciated that various sizes and shapes of conductive elements, thicknesses of barrier layer 336, as well as various gaps 338 and coated sections 339 may be implemented in embodiments of the present invention. In one exemplary embodiment, a wire having a 25 micron diameter is coated with a barrier layer having an average thickness that is approximately 3-10 microns. In such embodiments, uncoated gaps may have a length of approximately 2-5 millimeters, and the coated sections may have a length of 200-300 millimeters. In specific embodiments, uncoated gaps may have a length of 2.5 millimeters, and coated sections may have a length of approximately 250 millimeters.

As noted above, wire 332 is wound around coating frame 330 under tension. In certain embodiments, wire 332 may be manually wound around coating frame 332. As used herein, manual winding of wire 332 includes the use of one or tools (jigging, etc.) that facilitate the winding. In alternative embodiments, wire 332 may be wound around coating frame 330 using a winding system, such as winding system 490 illustrated in FIG. 4.

Figure 4:
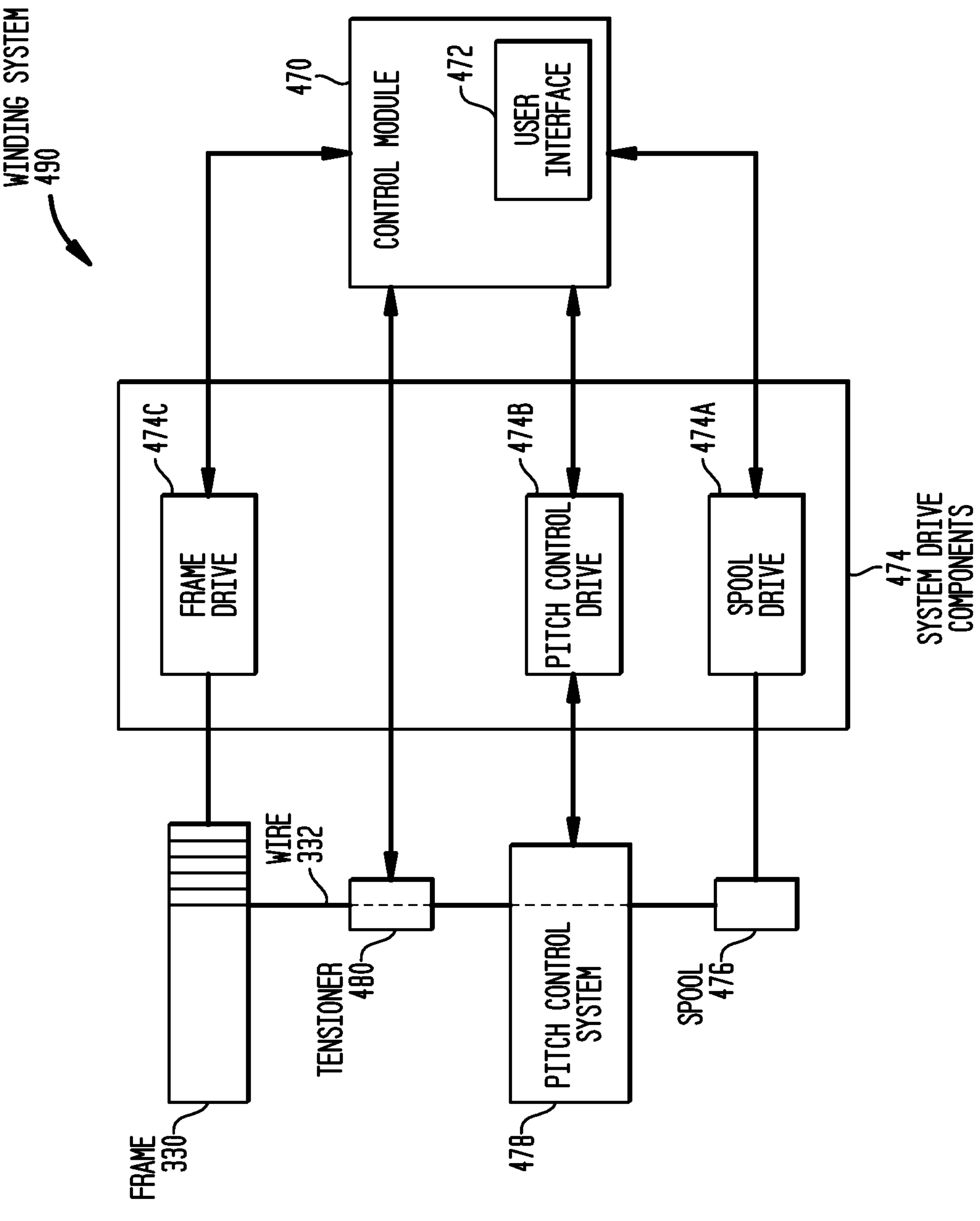
FIG. 4 is a schematic block diagram of a wire winding system that may be used to wind a wire around a coating frame, in accordance with embodiments of the present invention.

As shown in FIG. 4, winding system 490 comprises a pitch control system 478, and a tensioner 480 that transfer wire 332 from a spool 476 to coating frame 330. It would be appreciated that winding system 490 may also be used to transfer wire 332 from coating frame 330 to spool 476.

In the embodiments of FIG. 4, pitch control system 478 converts the pitch of the wire from spool 476 to a pitch for winding on to coating frame 330. Tensioner 480 controls the tension of wire 332 as it is wound around coating frame 330. Tensioner 330 is configured to ensure that the wire 332 is not placed under a tensile force that would damage or break wire 332, but with a sufficient tension that the wire remains substantially stationary during deposition.

As shown in FIG. 4, winding system 490 includes system drive components 474, comprising spool drive 474A, pitch control 474B and coating frame drive 474C, that electrically and/or mechanically control(s) the movement or operation of spool 476, pitch control system 478 and coating frame 330, respectively. Spool drive 474A, pitch control drive 474B and coating frame drive 474C receive control signals from control module 470. Tensioner 480 mechanical controls the tension of wire 332 and receives control signals directly from control module 470. As shown, control module 470 includes a user interface 472.

Figure 5:
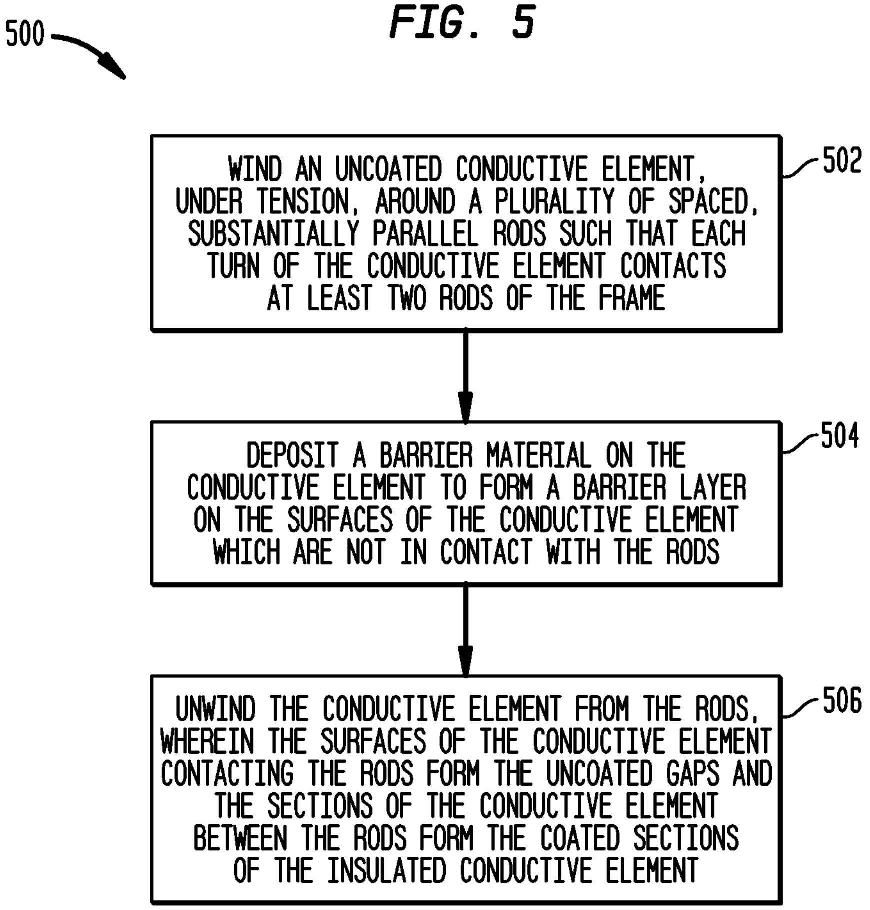
FIG. 5 is a flowchart illustrating the operations performed to form an elongate conductive element in accordance with embodiments of the present invention.

FIG. 5 is a flowchart illustrating a process 500 for coating an elongate, uncoated conductive element with a barrier layer to form an insulated conductive element of the present invention. The insulated conductive element comprises substantially continuously coated elongate sections separated by uncoated gaps which are substantially small relative to the lengths of the coated sections.

Process 500 begins at block 502 at which an uncoated elongate conductive element is wound, under tension, around a plurality of spaced, substantially parallel rods such that each turn of the conductive element contacts at least two rods of the coating frame. Process 500 continues at block 504 at which a barrier material is deposited on the conductive element to form a barrier layer on the surfaces of the conductive element which are not in contact with the rods. At block 506, the conductive element is unwound from the coating frame. The surfaces of the conductive element that were in contact with the rods during deposition form the uncoated gaps, while the sections of the conductive element between the rods form the coated sections of the insulated conductive element.

As described above, the embodiments of FIGS. 3A-3F were primarily been described with reference to a coating frame 330 comprising a plurality of spaced rods 334 extending between substantially parallel bases 320. It would be appreciated that alternative coating frames may also be implemented in embodiments of the present invention. FIGS. 6A-6E illustrate specific alternative embodiments.

Figure 6A:
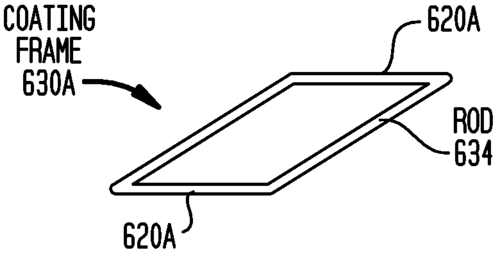
FIG. 6A is a perspective view of a coating frame in accordance with embodiments of the present invention.

In the embodiments of FIG. 6A, coating frame 630A has opposing bases 620A each comprising a single elongate member. Extending between opposing edges of bases 620A are two substantially parallel rods 634. Thus, in this embodiment coating frame 630A has a substantially planar shape.

Figure 6B:
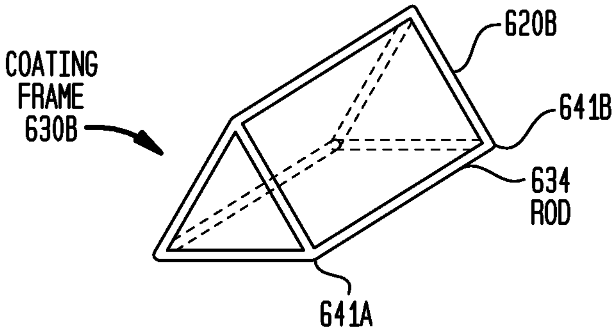
FIG. 6B is a perspective view of a coating frame in accordance with embodiments of the present invention.

FIG. 6B illustrates another embodiment of the coating frame of the present invention in which a coating frame 630B has opposing bases 620B each comprising three elongate members arranged to have a triangular configuration. Extending between the opposing vertices 641 of bases 620B are three substantially parallel rods 634.

Figure 6C:
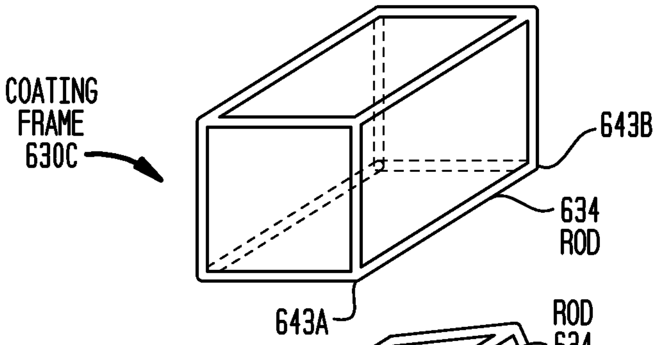
FIG. 6C is a perspective view of a coating frame in accordance with embodiments of the present invention.

Furthermore, in the embodiments of FIG. 6C, a coating frame 630C has opposing bases 620C each comprising four elongate members arranged in a rectangular configuration. Extending between the opposing vertices 643 of bases 620C are four substantially parallel rods 634.

Figure 6D:
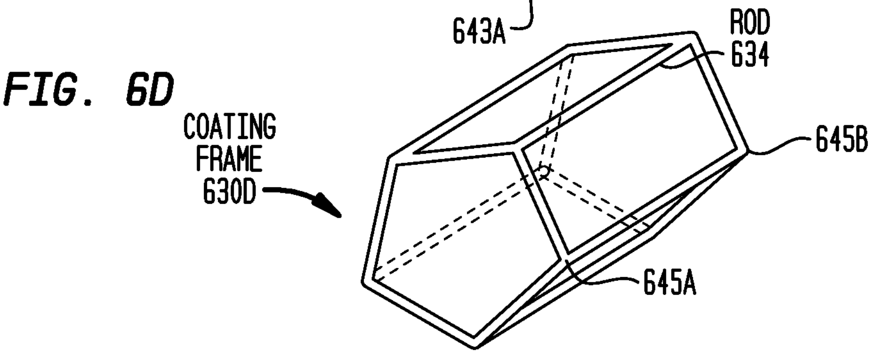
FIG. 6D is a perspective view of a coating frame in accordance with embodiments of the present invention.

FIG. 6D illustrates further embodiments in which coating frame 630D has opposing bases 620D each comprising five elongate members arranged in a pentagonal configuration. Extending between the opposing vertices 645 of bases 620D are five substantially parallel rods 634.

Figure 6E:
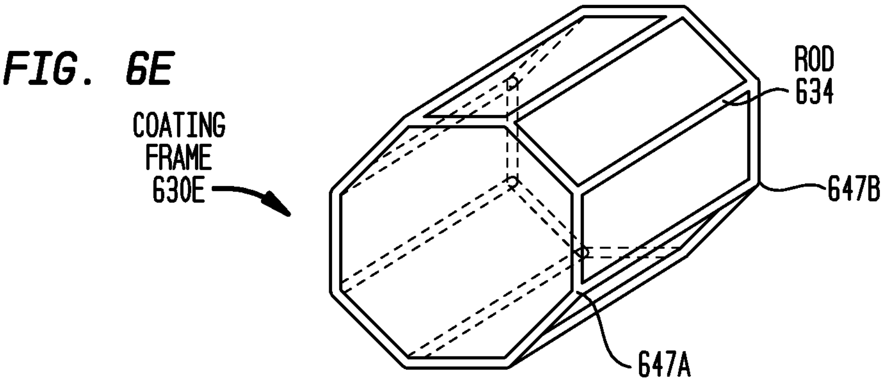
FIG. 6E is a perspective view of a coating frame in accordance with embodiments of the present invention.

In the embodiments of FIG. 6E, coating frame 630E has opposing bases 620E each comprising eight elongate members arranged in an octagonal configuration. Extending between the opposing vertices 647 of bases 620E are eight substantially parallel rods 634.

As noted, FIGS. 6A-6E illustrate embodiments in which a coating frame 630 comprises two, three, four, five and eight substantially parallel rods 634, respectively. It would be appreciated that greater number of rods arranged in a variety of positions may be implemented in embodiments of the present invention. Thus, the above embodiments would be considered illustrative and do not limit the present invention. It would also be appreciated that bases 620 are not limited to the use of arranged elongated members and may be formed, for example, from a planar element such as a sheet of metal, plastic, etc.

Figure 7A:
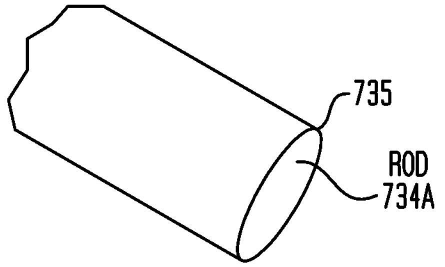
FIG. 7A is a perspective view of a section of a coating frame rod in accordance with embodiments of the present invention.

The above aspects of the present invention have been generally illustrated with reference to tubular rods having a generally circular cross-sectional shape. Rods having alternative cross-section shapes may also be utilized to maintain the strength of the rod while minimizing the contact length between a wire and a rod. As described above, minimizing the contact length between a wire and a rod minimizes the gaps that are formed in the barrier layer. FIGS. 7A-7D illustrate specific alternative rods having different cross-sectional shapes. Specifically, FIG. 7A illustrates a rod 734A having an oval cross-sectional shape. In such embodiments, rod 734A would be positioned within a coating frame such that a wire wound there around is in contact with one of the ends 735 positioned on the long axis of the oval.

Figure 7B:
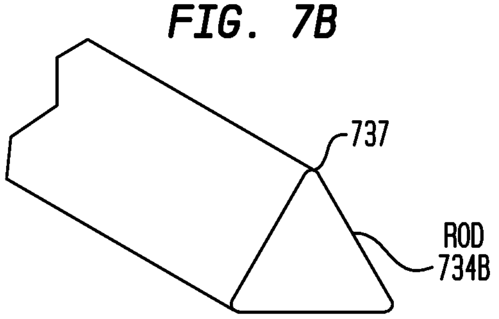
FIG. 7B is a perspective view of a section of a coating frame rod in accordance with embodiments of the present invention.

FIG. 7B illustrates another alternative embodiment in which a rod 734B has a generally triangular cross-sectional shape. In such embodiments, rod 734B is positioned in a coating frame such that the wire contacts rod 734B at the rounded apex 737 of the rod. Apex 737 has a radius of curvature that ensures that apex 737 does not have sharp edges that may potentially damage a wire in contact therewith.

Figure 7C:
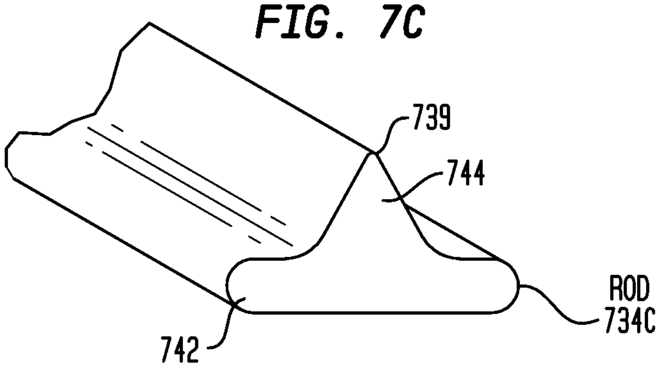
FIG. 7C is a perspective view of a section of a coating frame rod in accordance with embodiments of the present invention.

FIG. 7C illustrates a still further embodiment in which rod 734C has a triangular portion 744 extending from an oblong portion 742. Rod 734C is positioned in a coating frame such that the wire contacts rod 734C at the rounded apex 737 of triangular portion 744.

Figure 7D:
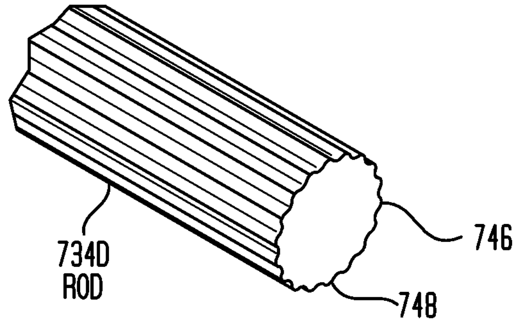
FIG. 7D is a perspective view of a section of a coating frame rod in accordance with embodiments of the present invention.

FIG. 7D illustrates a yet another embodiments in rod 734D has an undulating surface 746 comprising a plurality of rounded projections 748. When positioned within a coating frame, a wound wire contacts one or more rounded projections 748. As noted above, embodiments of the present invention are directed to forming an insulated conductive element comprising substantially continuously coated elongate sections separated by uncoated gaps which are substantially small relative to the lengths of the coated sections. In the embodiments of FIG. 7D, when the wire contacts two or more rounded projections 748, the gap extends between the locations where the wire contacts the first rounded projection 748, and the point where the wire contacts the last rounded projection 748 before extending to a subsequent rod. Because the wire is separated from rod 734D between rounded projections, sections of coating may be formed within the gap. As used herein, a gap having sections of coating therein, such as the gaps formed using rod 734D, is referred to as an uncoated gap.

As noted, the above embodiments of the present invention are generally directed to forming an insulated conductive element having a barrier layer comprising substantially continuously coated sections separated by uncoated gaps. The uncoated gaps have a length that is substantially small relative to the lengths of the coated sections. In certain above embodiments of the present invention, the uncoated gaps are generally disposed at known lengths, resulting in coated sections of known length. Furthermore, as used herein, a substantially continuous section refers to a continuous coating applied to those surfaces not in contact with a coating frame that may include minor imperfections resulting from the variability of a vapor deposition process or subsequent usage.

Further embodiments of the present invention described below are generally directed to forming an insulated conductive element having a substantially continuous barrier layer extending the length thereof. Similar to the embodiments described above, a substantially continuous barrier layer refers to a continuous coating applied to the length of the conductive element that may include minor imperfections resulting from the variability of a vapor deposition process or subsequent usage.

Figure 8:
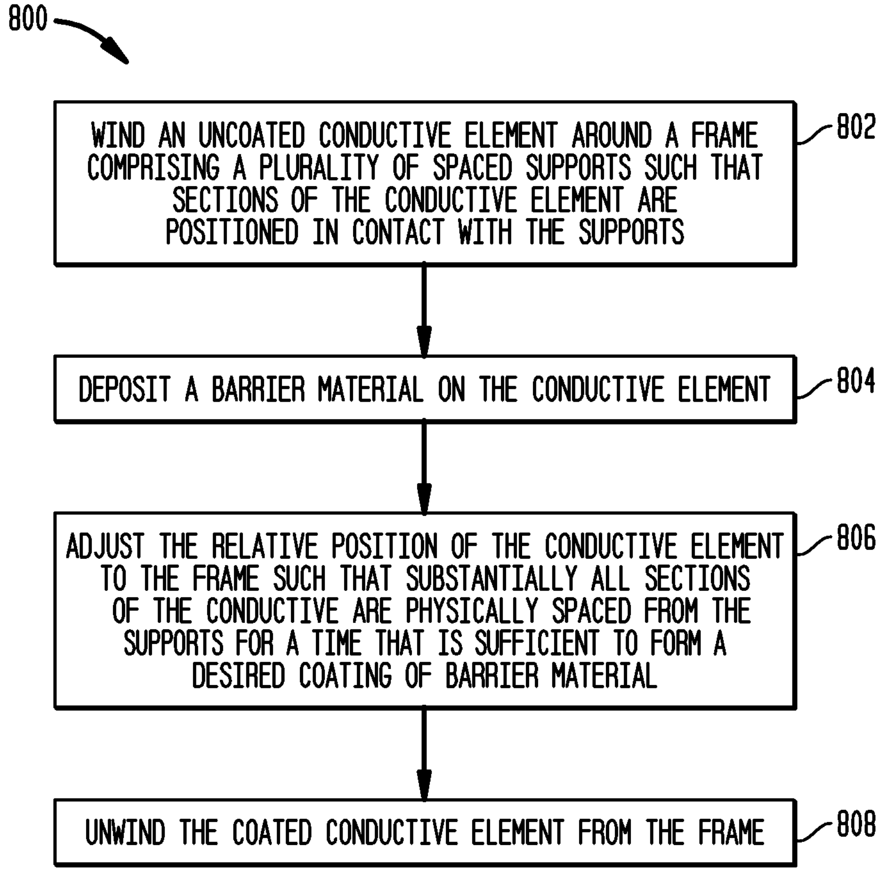
FIG. 8 is a flowchart illustrating the operations performed to form an elongate conductive element in accordance with embodiments of the present invention.

FIG. 8 illustrates a first method 800 of coating an elongate, uncoated conductive element with a substantially continuous barrier layer. The method begins at block 802 at which an uncoated conductive element is wound around a coating frame. The coating frame comprises a plurality of spaced supports, and the conductive element is wound around the coating frame such that sections of the conductive element are positioned in contact with the supports.

The method continues at block 804 at which a barrier material is deposited on the conductive element. At block 806, during deposition of the barrier material, the relative position of the conductive element to the coating frame is adjusted so that substantially all sections of the conductive element are physically separated from the supports for a time that is sufficient to form the substantially continuous barrier layer. In other words, at least one of the conductive element and the coating frame are moved relative to another during deposition. This relative movement results in each section of the conductive element being exposed for coating with the barrier material. At block 808, the insulated conductive element is unwound from the coating frame.

FIGS. 9A-15 illustrate various apparatus that may be employed to move a conductive element relative to a coating frame during the method of FIG. 8. For ease of description, FIGS. 9A-15 will be described with reference to a conductive element in the form of a single strand wire. It would be appreciated that other types of conductive elements such as multi-strand wires, conductive ribbons, shim or carbon nano tube (CNT) yarns, etc. may also be utilized in these embodiments of the present invention.

Figure 9A:
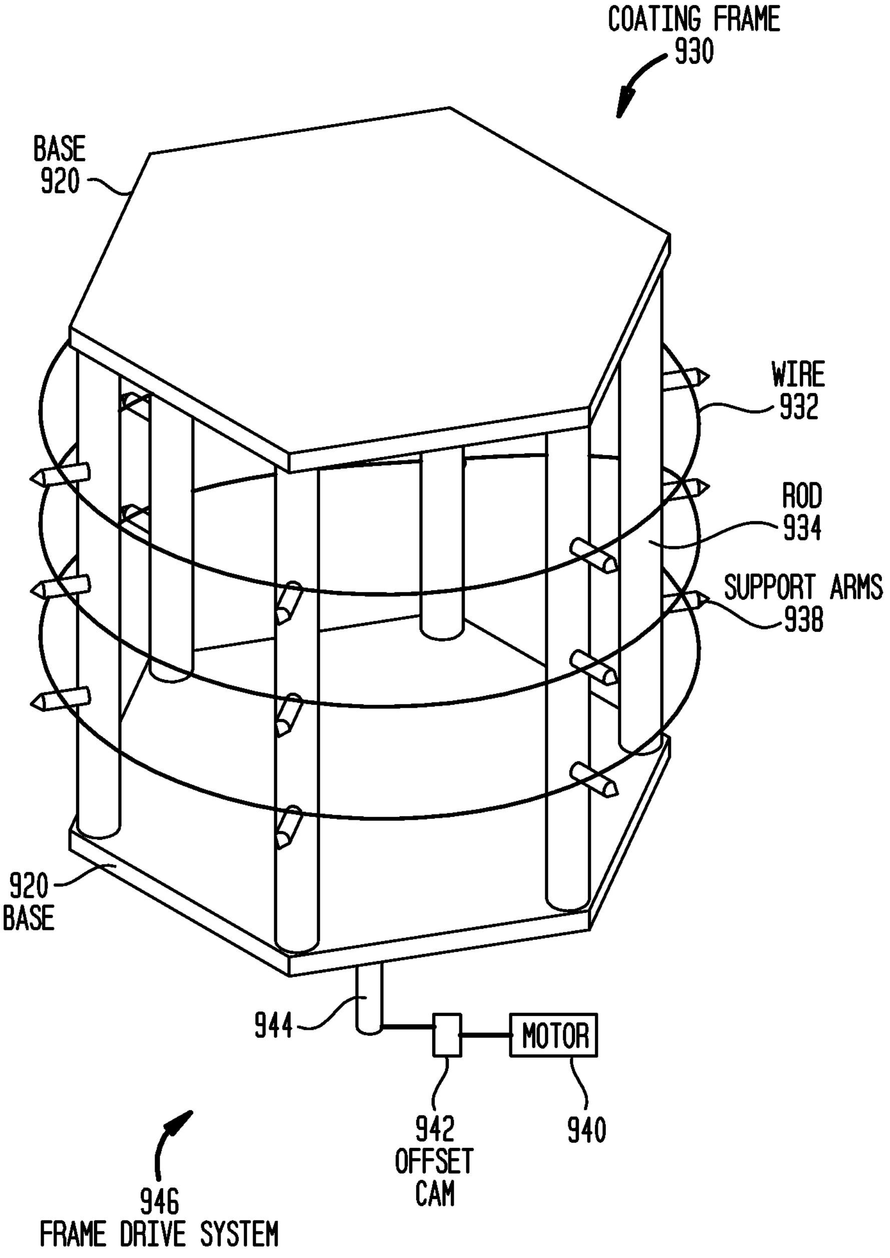
FIG. 9A is a perspective view of a coating frame connected to a coating frame drive system in accordance with embodiments of the present invention.

FIG. 9A is perspective view of a coating frame 930 that may be implemented in embodiments of the present invention. As shown, coating frame 930 comprises opposing bases 920 having substantially parallel rods 934 extending there between. Extending from rods 934 are a plurality of elongate, spaced radial support arms 938. A wire 932 may be loosely wound around coating frame 930 such that the wire is supported by the elongate surface of support arms 938.

As noted above, a barrier layer is deposited on wire 932 to form an insulated conductive element. The barrier layer may be deposited on wire 932 through the use of a vapor deposition apparatus, such as apparatus 150 of FIG. 1. FIG. 9A illustrates specific embodiments of a coating frame 930 that, once positioned in a deposition chamber such a deposition chamber 104, is connected to a coating frame drive system 946 via a coupling member 944. In the embodiments of FIG. 9A, coating frame drive system 946 comprises a motor 940 that rotates coupling member 944 and coating frame 930 during the coating process. In certain embodiments, coating frame drive system 946 also comprises an offset cam 942. Offset cam 942 produces a non-circular rotation of member 944 that causes vibration of coating frame 930 during rotation. Because wire 932 is loosely wound around coating frame 930, the vibration induced by offset cam 942 causes movement of the wire relative to the coating frame. More specifically, as a result of the vibration, substantially all sections of wire 932 are physically separated from the supports for a time that is sufficient to form the substantially continuous barrier layer. In other words, the vibration results in each section of wire 932 being exposed for coating with the barrier material. Furthermore, because the vibration is random, a generally uniform barrier layer is formed on the wire.

As noted above, coating frame 930 comprises a plurality of support arms 938 extending from rods 934. Each support arm 938 is separated from an adjacent support arm 938 by a horizontal distance 982, and a vertical distance 980. Due to the continual vertical change between adjacent support arms 938, the wound wire 932 follows an inclined helical path around coating frame 930. The sloped pathway followed by wire 932 between adjacent support arms 938 is referred to as pitch or slope of the wire.

When coating wire 932, the turns of the wire remain physically separate from one another during deposition. Therefore, the pitch of wire 932 versus the number of supports arms 938 is controlled to reduce the probability of the adjacent turns coming into contact with each other during deposition. The pitch of the wire (that is, the pitch between adjacent supports) is also a factor to ensure that there is sufficient spacing for winding the wire, cleaning of the coating frame after deposition, etc. Furthermore, support arms 938 having a length that, when wire 932 is positioned thereon, is sufficiently large that vibration of coating frame 930 likely does not cause wire 930 to contact rods 934. For example, in certain embodiments, to form a barrier layer having a thickness of 5-7 microns on a 25 micron wire, a support arm of 25 mm length is used. In such embodiments, wire 932 is positioned approximately 10 mm from rod 934. The 15 mm extension of the support arm from the position of wire 932 ensures that wire 932 does entirely separate from the support arm as a result of the vibration.

Figure 9B:
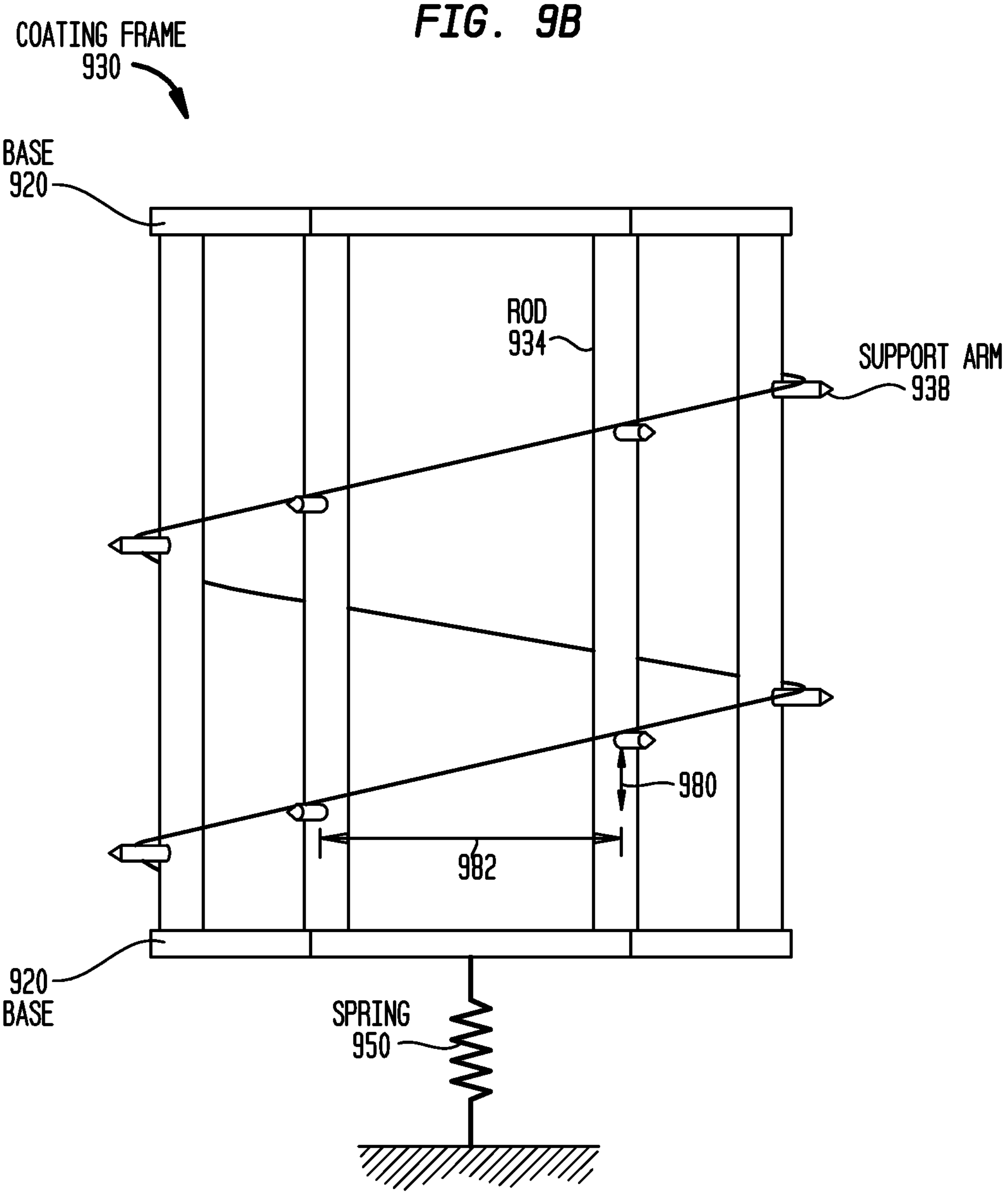
FIG. 9B is a side view of the coating frame of FIG. 9A connected to a spring in accordance with embodiments of the present invention.

As noted above, in the embodiments of FIG. 9A, coating frame 930 is coupled to a coating frame drive system 946 that causes vibration of coating frame 930, thereby resulting in movement of wire 932 relative to coating frame 930. In the embodiments of FIG. 9B, once positioned in a deposition chamber, coating frame 930 is coupled to a spring 950 that facilitates vibration of coating frame 930. In certain embodiments, spring 950 may be driven by a motor to induce the vibration. In alternative embodiments, spring 950 transfers and/or amplifies inherent vibration of the deposition apparatus to coating frame 930. Alternatively, the inherent vibration in the deposition apparatus could be increased by removing some of the existing dampening elements, or altering the location of the vacuum pump so that vibration of the pump vibrates the chamber.

Figure 9C:
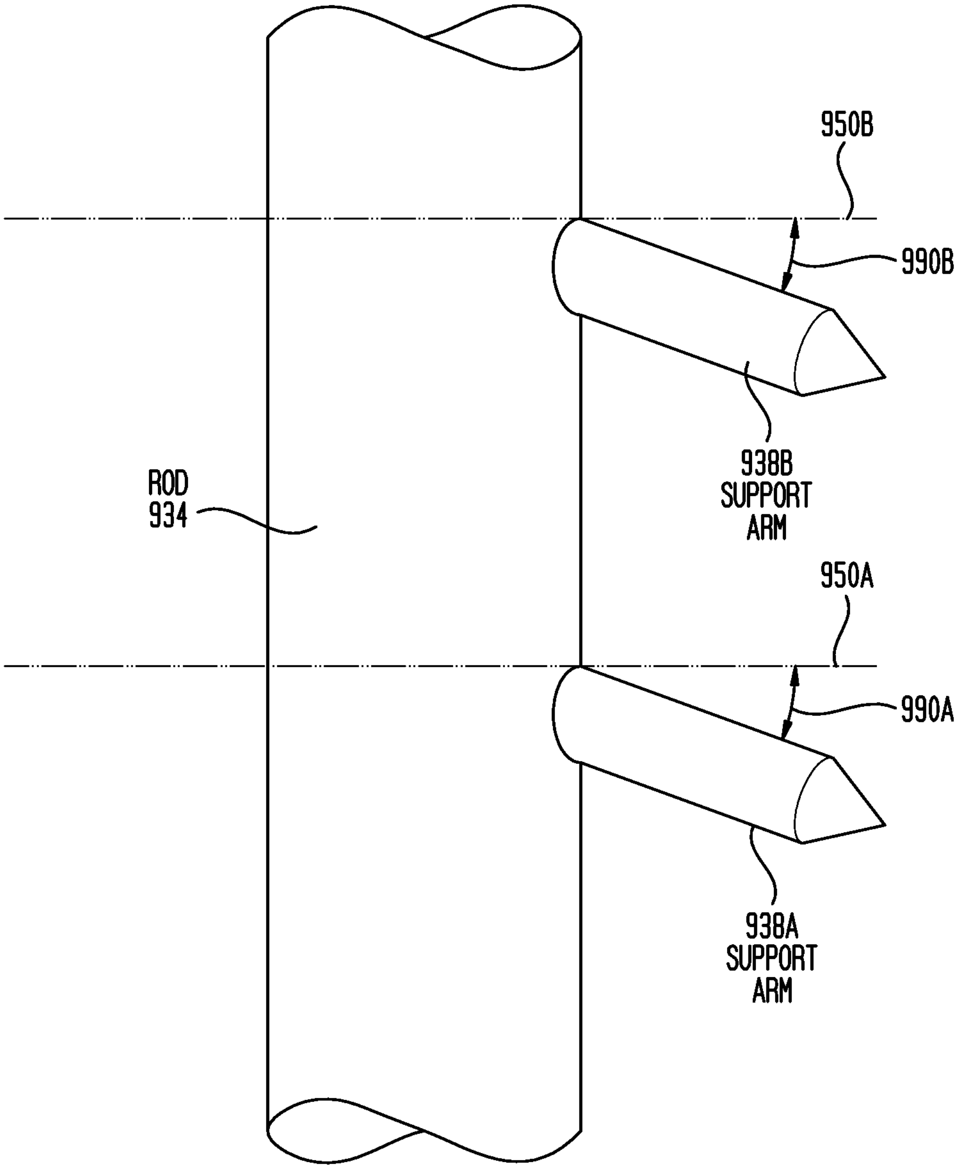
FIG. 9C is a side view of a coating frame rod and a pair of support arms of FIG. 9A in accordance with embodiments of the present invention.

FIG. 9C is a side view of two support arms 938 extending from a rod 934. In this illustrative embodiment, support arms each extend from rod 934 at a downward angle 990. Downward angle 990, which is measured with respect to a horizontal axis 950 extending through rod 934 at the base of each support arm 938, helps to prevent wire 930 from migrating towards rod 934 as a result of vibration. It would be appreciated that angle 990 varies in alternative embodiments.

It would be appreciated that various configurations for coating frame 930 are within the scope of the present invention. In one exemplary configuration, a coating frame has rods of 400 mm in length. Each rod includes support arms of 25 mm length, extending from the rod at a downward angle of 30 degrees. With a spacing of 3.5 mm between the distal end of an upper support arm and the base of a lower support arm, a total of 20 supports arms may be provided on each rod. Using these exemplary dimensions, the coating frame may support approximately 25 m of wire. It would be appreciated that the length of supported wire may be increased by decreasing the downward angle of the support arms, decreasing vertical spacing between support arms, increasing the rod height, etc. For example, a 400 mm rod having support arms of 2.5 mm in length at an angle of 0 degrees, and 0.5 mm spacing and a 3 mm wire pitch may support approximately 160 m of wire.

Figure 10:
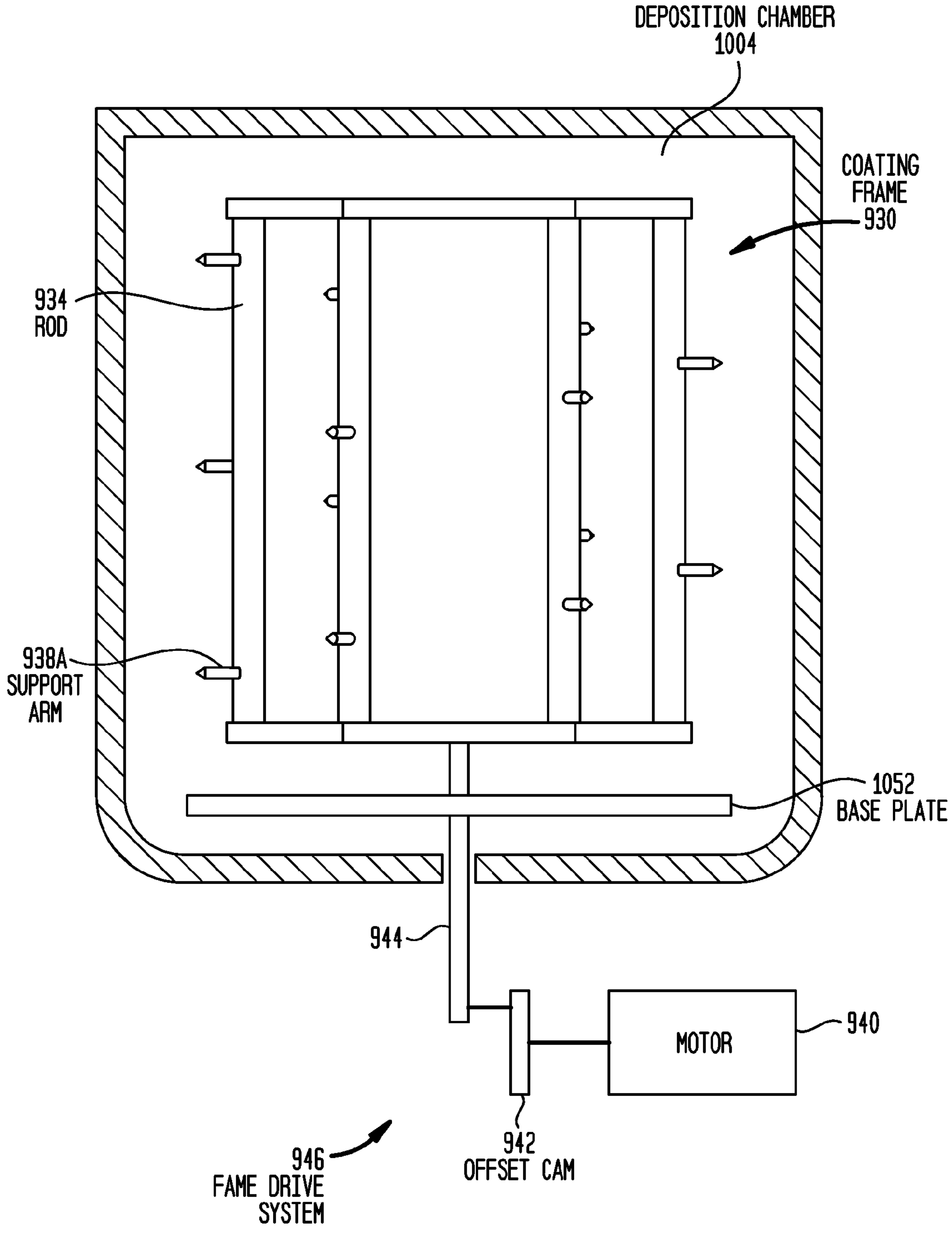
FIG. 10 is cut away view of a deposition chamber having the coating frame of FIG. 9A therein, in accordance with embodiments of the present invention.

FIG. 10 is cut-away view of a deposition chamber 1004 having an embodiment of coating frame 930 described above positioned therein. In these embodiments, coating frame 930 is connected to a base plate 1052. Similar to the embodiments of FIG. 9A, base plate 1052 is connected to a coating frame drive system 946 positioned outside of chamber 1004 via coupling member 944. As described above, motor 940 rotates coating frame 930, and offset cam 942 induces vibration of the coating frame during the rotation.

FIGS. 9A-10A have been described with reference to support arms 938 having a generally cylindrical shape terminating in a distal tip. It would be appreciated that other shaped support arms may be used in alternative embodiments of the present invention. For example, a support arm of the present invention may have any of the cross-sectional shapes described above with reference to FIGS. 7A-7D.

Furthermore, FIGS. 9A-10 illustrate embodiments of the present invention using a particular coating frame 930. FIGS. 11-15C illustrate additional coating frames that may be implemented in embodiments of the present invention.

Figure 11:
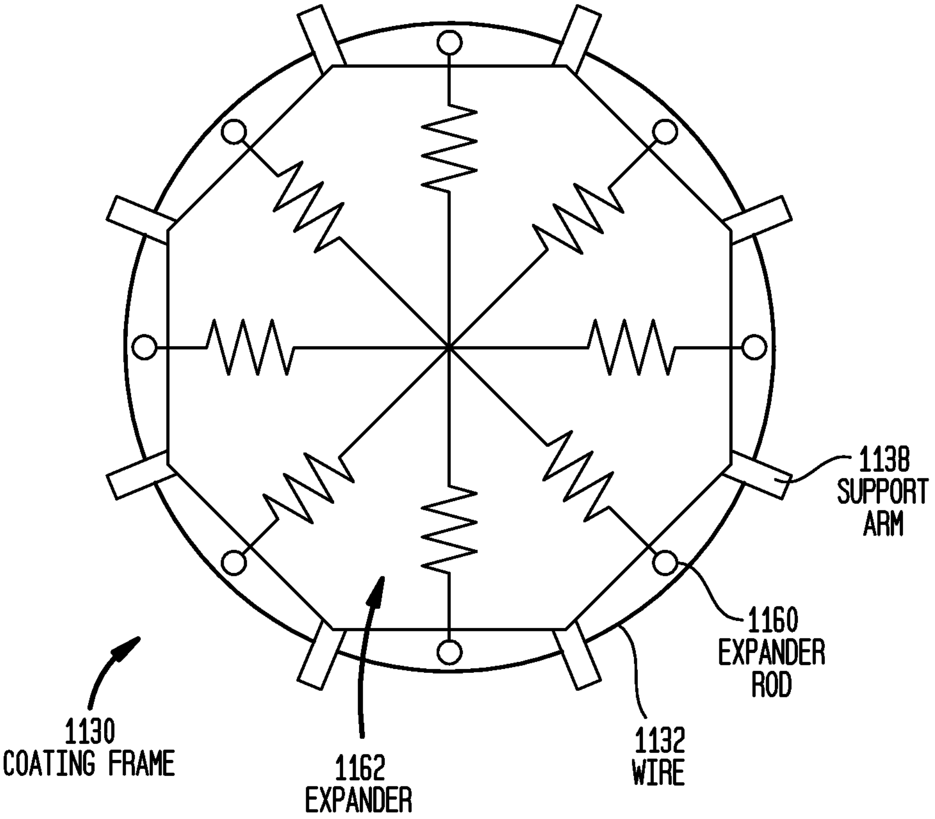
FIG. 11 is a top view of an expandable coating frame in accordance with embodiments of the present invention.

FIG. 11 is a top view of one alternative coating frame, referred to as expandable coating frame 1130. As shown in FIG. 11, coating frame 1130 comprises rods 1160 attached to an expander 1162 which allows the rods to move from a collapsed position to an open or expanded position. When expander 1162 is in the open position, shown in FIG. 11, wire 1132 is wound in tension around coating frame 1130 so that the wire is positioned adjacent to support arms 1138 and expander rods 1160.

As noted, FIG. 11 is a top view of expandable coating frame 1130. As such, wire 1132 is shown passing below the illustrated support arms 1138, and the wire is supported by arms 1132 that are not visible in FIG. 11 following removal of expander 1162.

Once winding of wire 1132 is completed, expander 1162 is collapsed in towards the center allowing wire 1132 reducing or relieving the tension in the wire, and expander may be removed. That is, wire 1132 is then loosely wound around collapsed coating frame 1132 and rather than being held tightly against rods 1160, wire 1138 is spaced from rods 1160. In this position, wire 1132 is free to move relative to coating frame 1130 during deposition.

Figure 12:
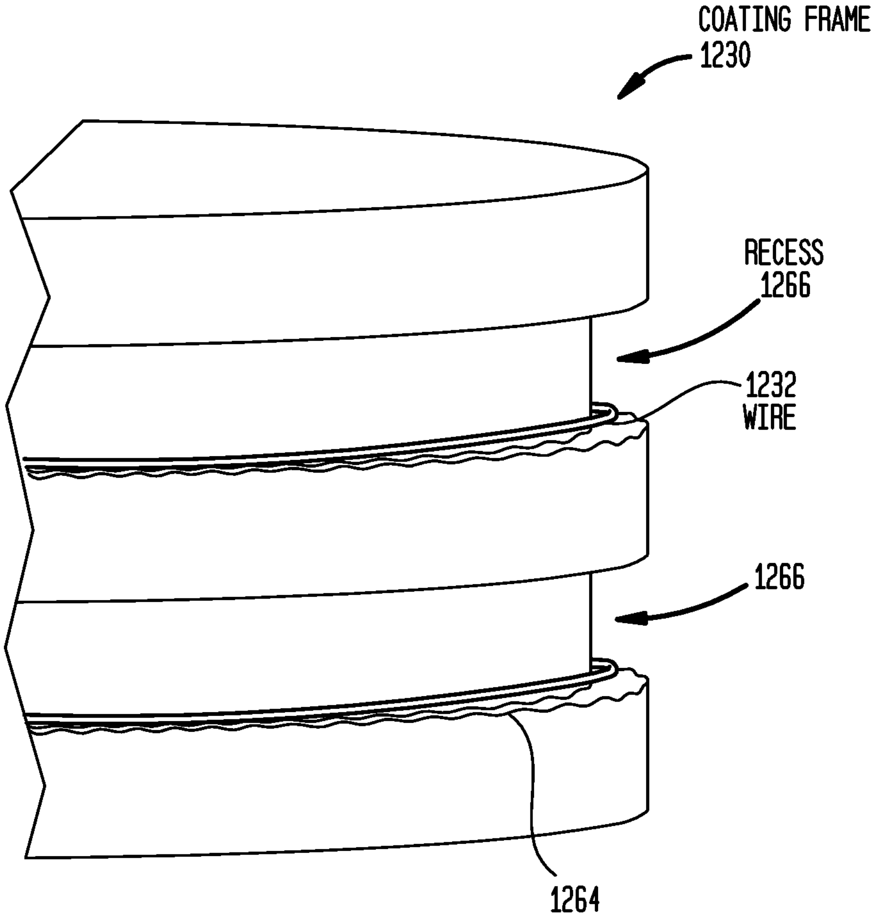
FIG. 12 is partial perspective view of a portion of a coating frame having recessed wire support regions, in accordance with embodiments of the present invention.

FIG. 12 is a partial perspective view of an alternative coating frame, illustrated at as coating frame 1230. In this embodiment, coating frame 1230 comprises a cylindrical member having a recess 1266 formed therein. Recess 1266 spirals about the circumference of coating frame 1230, and in this illustrative embodiment, has an undulating or wavy surface 1264. A wire 1232 is loosely wound around coating frame 1230 and is supported by undulating surface 1264. Similar to the embodiments described above, coating frame 1230 is vibrated during deposition so that wire 1232 moves with respect to coating frame 1230. Furthermore, because only discrete sections of wire 1232 are in contact with undulating surface 1264 at any time, movement of wire 1232 with respect to coating frame 1230 produces a substantially continuous barrier layer on the surface of the wire.

Figure 13A:
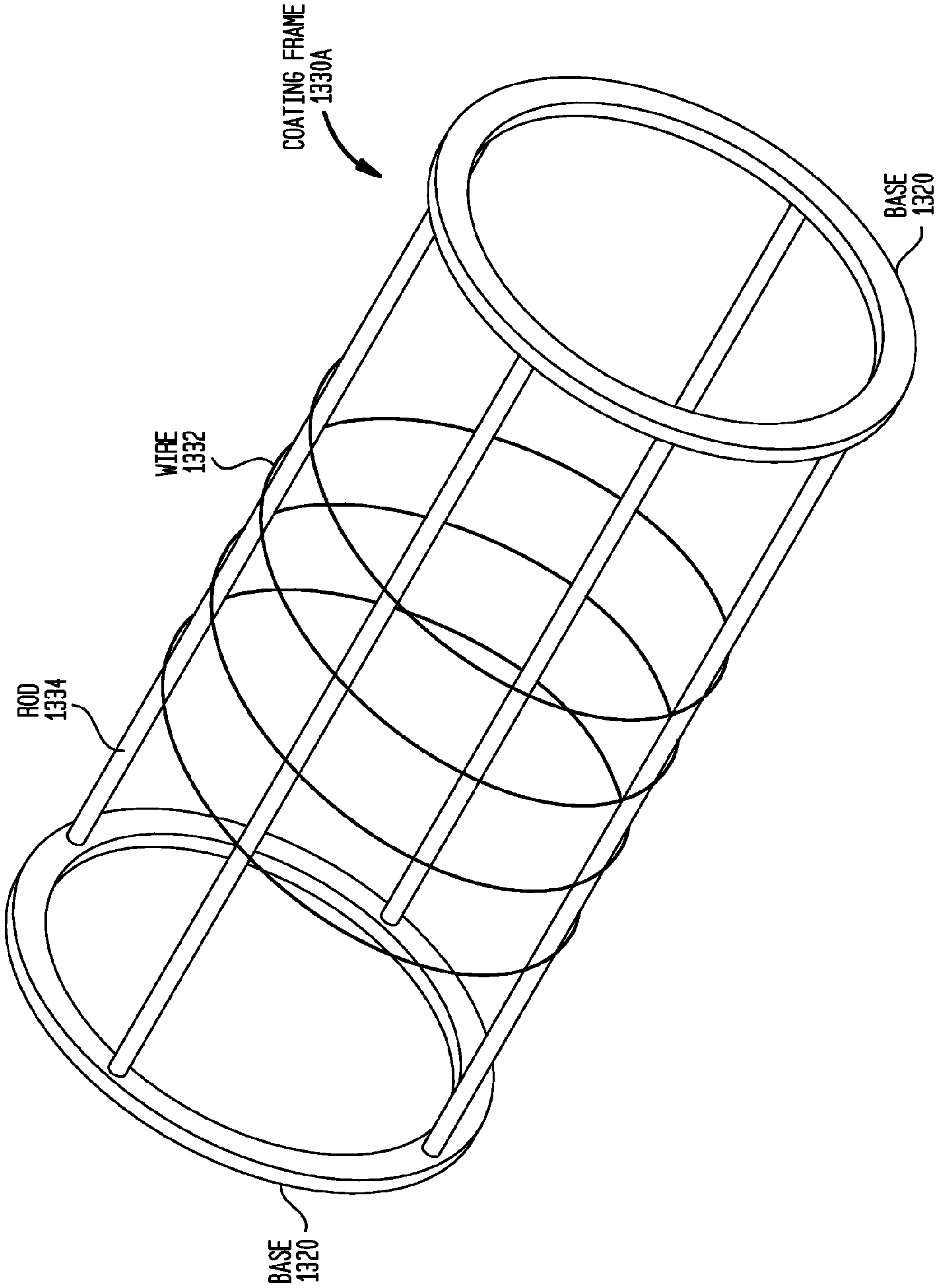
FIG. 13A is a perspective view of a coating frame in accordance with embodiments of the present invention.

FIG. 13A is a perspective view of another coating frame, illustrated as coating frame 1330A. Coating frame 1330A comprises opposing bases 1320, and a plurality of substantially parallel rods 1334 extending between the bases. In the illustrative embodiments of FIG. 13A, coating frame 1330A is positionable horizontally in a deposition chamber. That is, rods 1334 are configured to be positioned parallel to the bottom of the deposition chamber. In such embodiments, a vapor deposition apparatus having a horizontal deposition chamber may be utilized.

During deposition, coating frame 1330A and wire 1332 both rotate with respect to the deposition chamber. However, wire 1332 is wound around rods 1334 under a tension that causes coating frame 1330A to rotate at a speed that different than that of wire 1332. Therefore, during rotation, coating frame 1330A moves relative to wire 1332. Because coating frame 1330A moves relative to wire 1332 during deposition, sections of wire 1332 that are in contact with rods 1334 become physically separated from the rod. Those sections remain separated from the rod for a period of time that is sufficient to coat the sections with a desired thickness of barrier material. Thus, a substantially continuous barrier layer is formed on wire 1332.

In alternative embodiments of the present invention, rods 1334 may be flexible and have a sufficiently small diameter such that the rods are strong enough to support wire 1332, but have sufficient flexibility so that rods 1334 bend and/or move relative to wire 1332 during coating. Because wire 1332 does not follow the movement of an individual flexible rod 1334, the bending/movement of rods 1334 during coating provides additional physical separation between the rods those sections of wire 1332 previously in contact with rods 1334. Thus, the bending/movement of rods 1334 helps to ensure that all portions of wire 1332 are exposed during deposition so that a desired barrier layer is formed. Alternatively, rods 1334 may be formed by thin wires or strings (e.g. Polyurethane) stretched between bases 1320. In these embodiments, the individual string/wire bends or change location as a result of the vibration. As noted, wire 1332 does not does not follow the movement of an individual string or wire so that all surfaces of wire 1332 are coated with the barrier material.

Figure 13B:
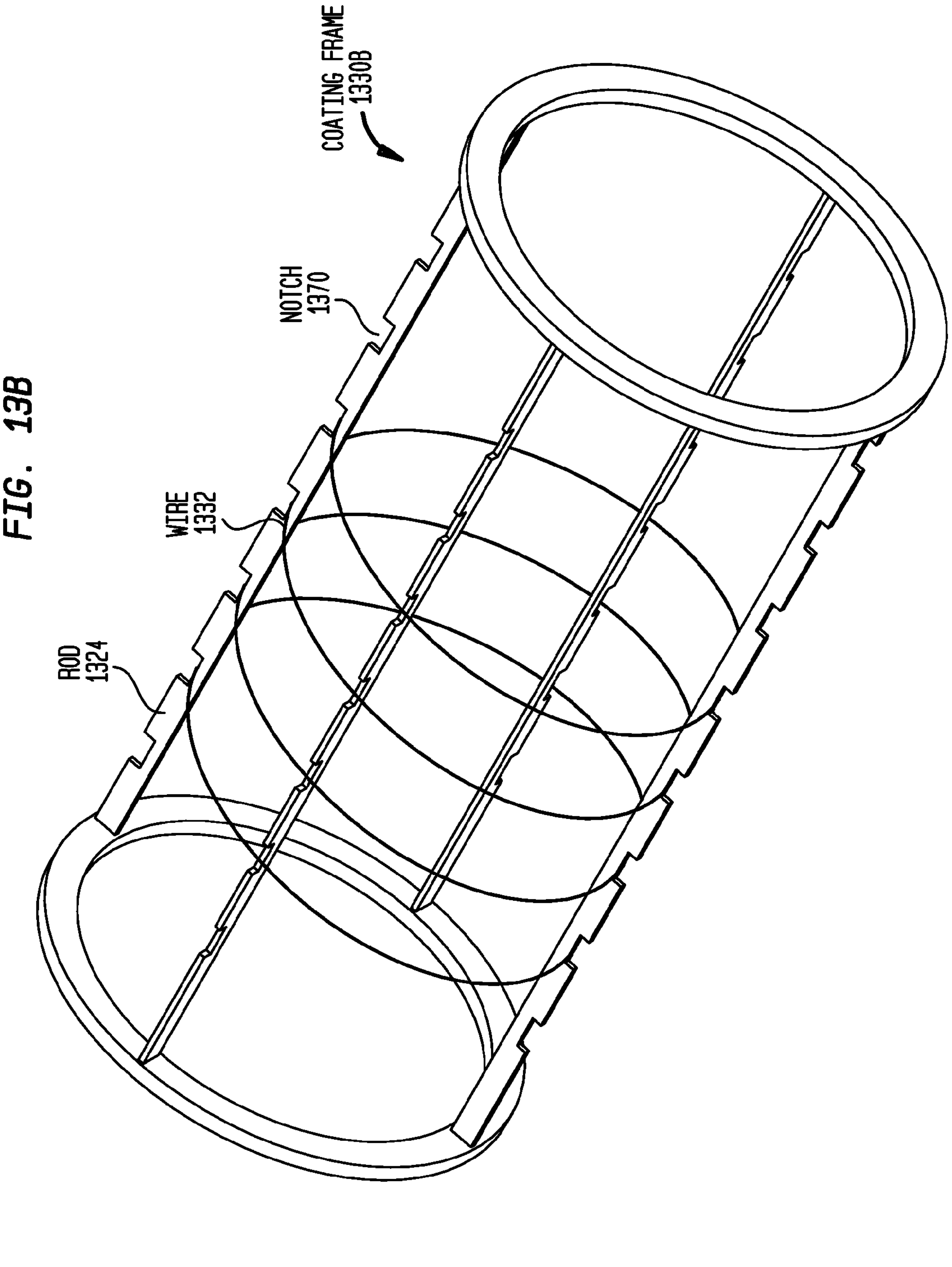
FIG. 13B is a perspective view of a coating frame in accordance with embodiments of the present invention.

FIG. 13B is a perspective view of another coating frame, illustrated as coating frame 1330B, positionable horizontally in a deposition chamber. Coating frame 1330B comprises opposing bases 1320, and a plurality of substantially parallel rods 1324 extending between the bases. Rods 1324 have a generally rectangular shape, and have a plurality of cut-outs or notches 1370 formed therein. Notches 1370 are aligned to create a channel extending about the circumference of frame 1330C. In these embodiments, wire 1332 is loosely around rods 1324 so that wire 1332 extends through the channel formed by notches 1370.

Similar to the embodiments described above, coating frame 1330B rotates about a substantially horizontal axis during deposition. As coating frame 1330B rotates and a rod 1324 moves towards the bottom of the chamber, the sections of loosely wound wire 1332 in contact with channels 1370 will separate from the rod. As these sections of wire 1332 become spaced from channels 1370, the barrier material will coat the sections of wire 1332 that were previously in contact with the channels, thereby creating a desired barrier layer on the wire.

Figure 13C:
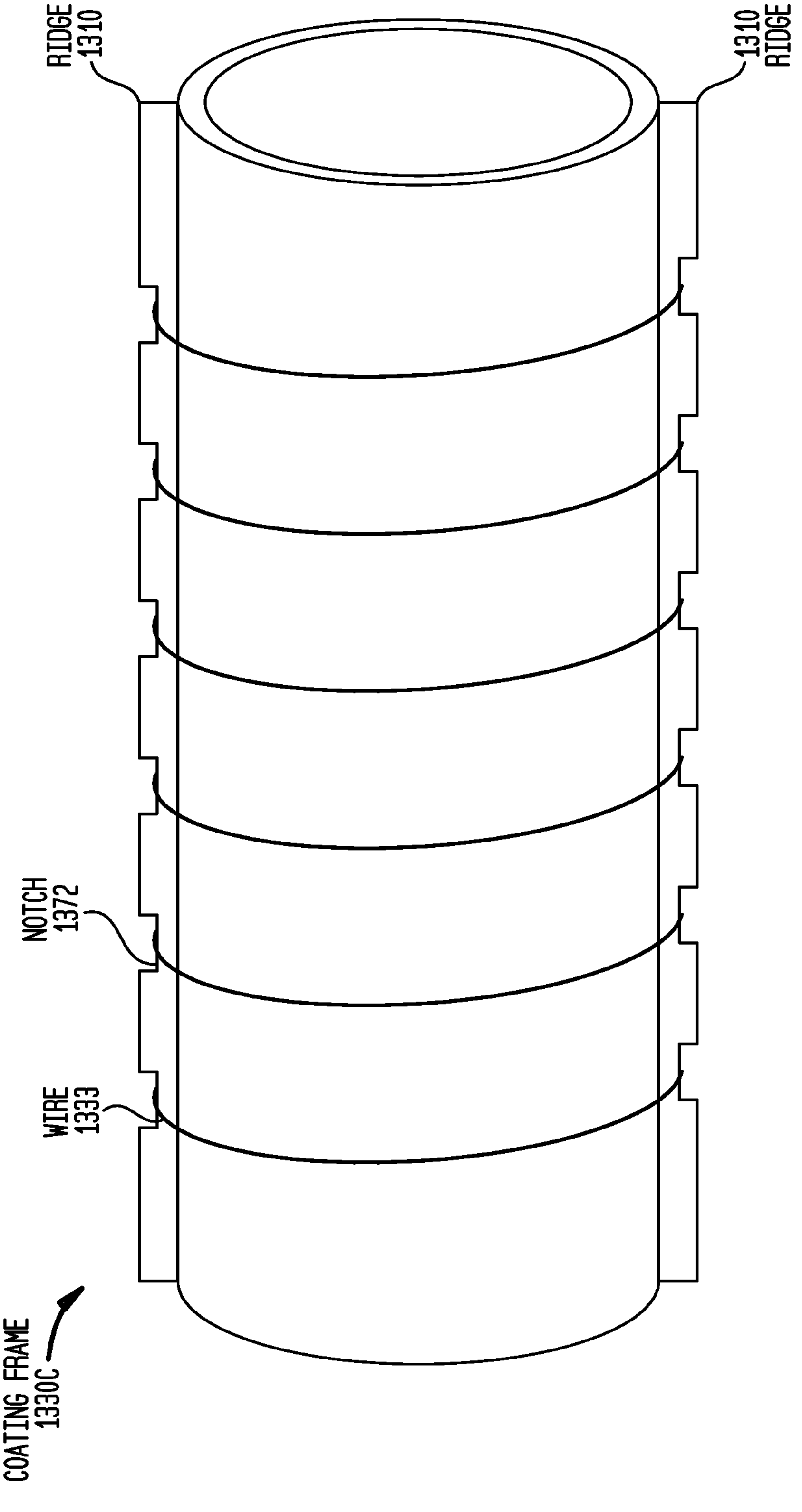
FIG. 13C is a perspective view of a coating frame in accordance with embodiments of the present invention.

FIG. 13C is a perspective view of a still other coating frame, illustrated as coating frame 1330C, configured to be positioned horizontally in a deposition chamber. Notches 1372 are aligned to create a channel extending about the circumference of frame 1330D. In these embodiments, coating frame 1330C comprises a tubular member having ridges extending along the length thereof. Ridges 1310 comprise a plurality of notches 1372 therein. In these embodiments, wire 1332 is loosely around frame 1330C so that wire 1332 extends through the channel formed by notches 1372.

Similar to the embodiments described above, coating frame 1330C rotates during deposition. As coating frame 1330C rotates and a ridge 1310 moves towards the bottom of the chamber, the sections of loosely wound wire 1332 in contact with notches 1372 will separate from the channel. As these sections of wire 1332 become spaced from channels 1372, the barrier material will coat the sections of the wire that were previously in contact with the channels, thereby creating a desired barrier layer on the wire.

In an alternative embodiment of FIG. 13C, coating frame 1330C may comprise a threaded shaft. In such embodiments, channels 1372 extend around the circumference of the shaft. Therefore, during rotation, sections of wire rotating towards the bottom of the deposition chamber continually separate from the portion of the shaft near the bottom of the chamber.

Figure 13D:
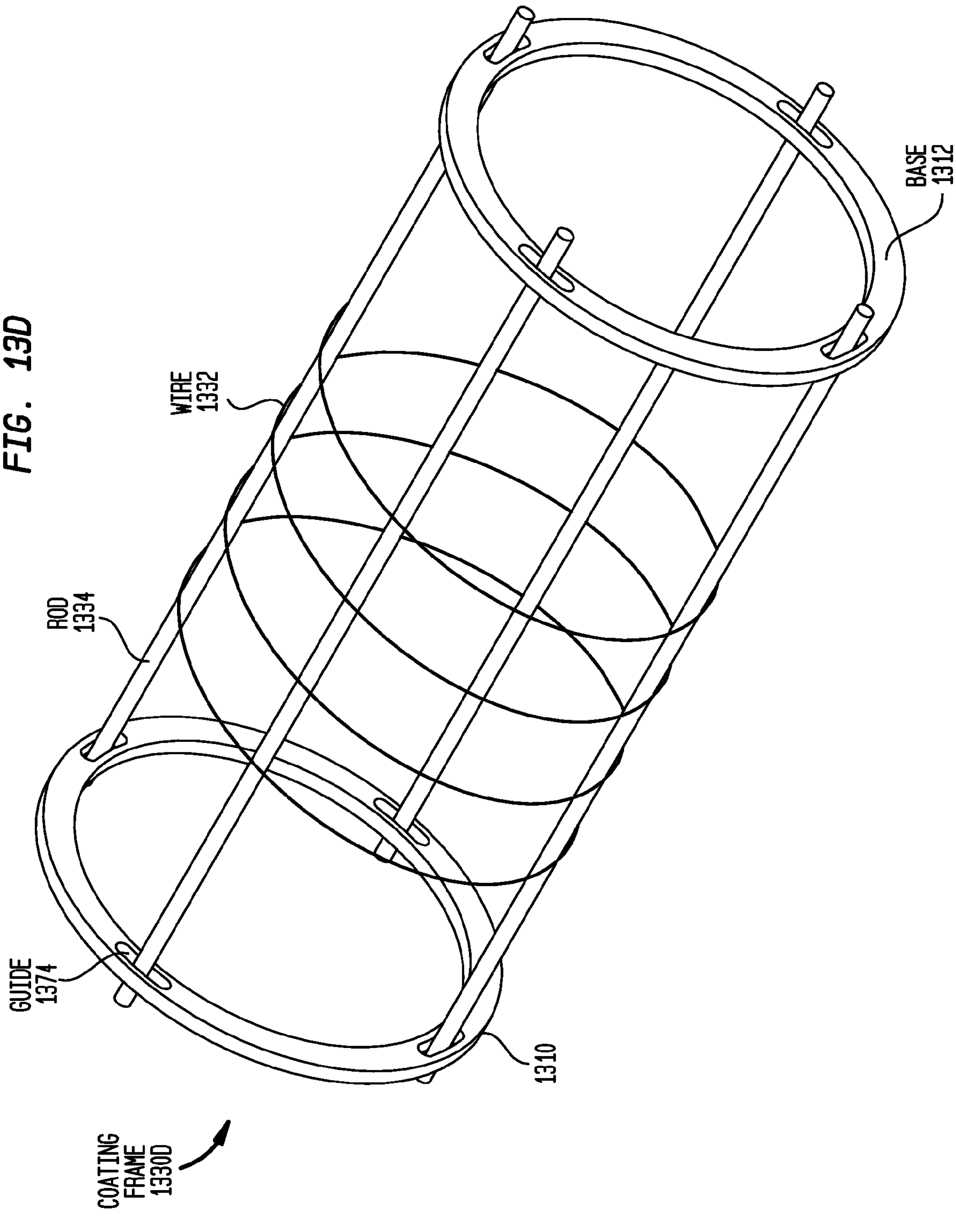
FIG. 13D is a perspective view of a coating frame in accordance with embodiments of the present invention.

FIG. 13D is a perspective view of a still other coating frame, illustrated as coating frame 1330D, configured to be positioned horizontally in a deposition chamber. Coating frame 1330D comprises opposing bases 1312, and a plurality of substantially parallel rods 1334 extending between the bases.

As shown, bases 1312 also comprise rod guides 1374. As coating frame 1330D rotates, the weight of rods 1334 causes the rods to move within guides 1374, thus alternating the location of rods 1334 with respect to wire 1332. It would be appreciated that rods 1334 can also rotate during their movement, facilitating minimal drag on wire 1332. Because rods move relative to wire 1332 during deposition, sections of wire 1332 that are in contact with a rods 1334 become physically separated from the rod. Those sections remain separated from the rod for a period of time that is sufficient to coat the sections with a desired thickness of barrier material. Thus, a substantially continuous barrier layer is formed on wire 1332.

Figure 14:
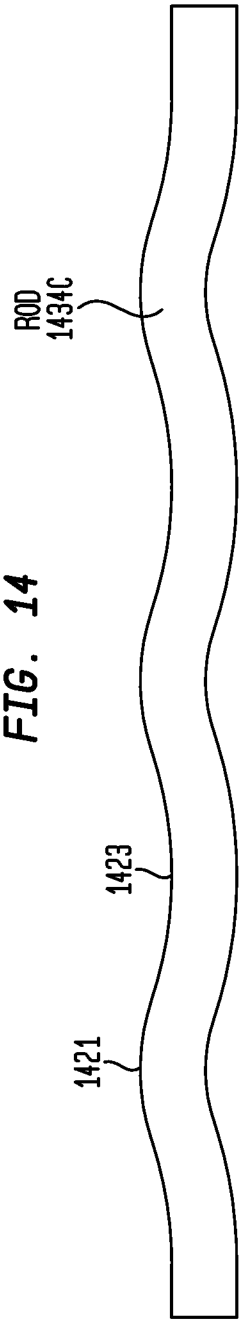
FIG. 14 is a side view of a coating frame rod in accordance with embodiments of the present invention.

The embodiments of FIGS. 13A and 13D have been illustrated with rods 1334 having a generally circular cross-sectional shape. It would be appreciated that rods 1334 may have other cross-sectional shapes in alternative embodiments of the present invention. For example, rods having any of the cross-sectional shapes illustrated in FIGS. 7A-7D may be implemented in other embodiments. FIG. 14 illustrates a still further embodiment of a rod 1434 having an undulating or wavy shape. More specifically, in the embodiments of FIG. 14, rod 1434 is flexible and comprises a series of spaced projections 1421. Adjacent projections 1412 are separated by concave regions 1423 to form an elongate undulating surface. The vertical spacing between the end of a projection 1421 and the center of an adjacent concave region 1423 is substantially small relative to thickness of a wire wound there around so as to impart minimal tension change on the wire during rotation. During deposition of an embodiment implementing rod 1434, the rod could rotate with respect to the coating frame bases, thereby providing relative movement between the rod and the wire wound around the coating frame. It would be appreciated that rod 1434 is not shown to the scale and the undulations may be smaller than those shown in FIG. 14. In certain embodiments, the undulations would not be visible in a to scale illustration. As such, the embodiments of FIG. 14 are merely illustrative and do not limit the scope of the present invention.

As noted above, in certain vapor deposition systems mechanical movement of various elements occurs during operation, thereby resulting in an inherent level of vibration of a coating frame. In the embodiments of FIGS. 13A-13D, this inherent vibration enhances the relative movement of coating frames 1330 to wire 1332. In alternative embodiments, the inherent vibration may be amplified using, for example, a spring. In other embodiments, additional vibration may also be added using, for example, the coating frame drive system described above with reference to FIG. 9A or through the application of high frequency (e.g. ultra sonic) vibration.

Figure 15A:
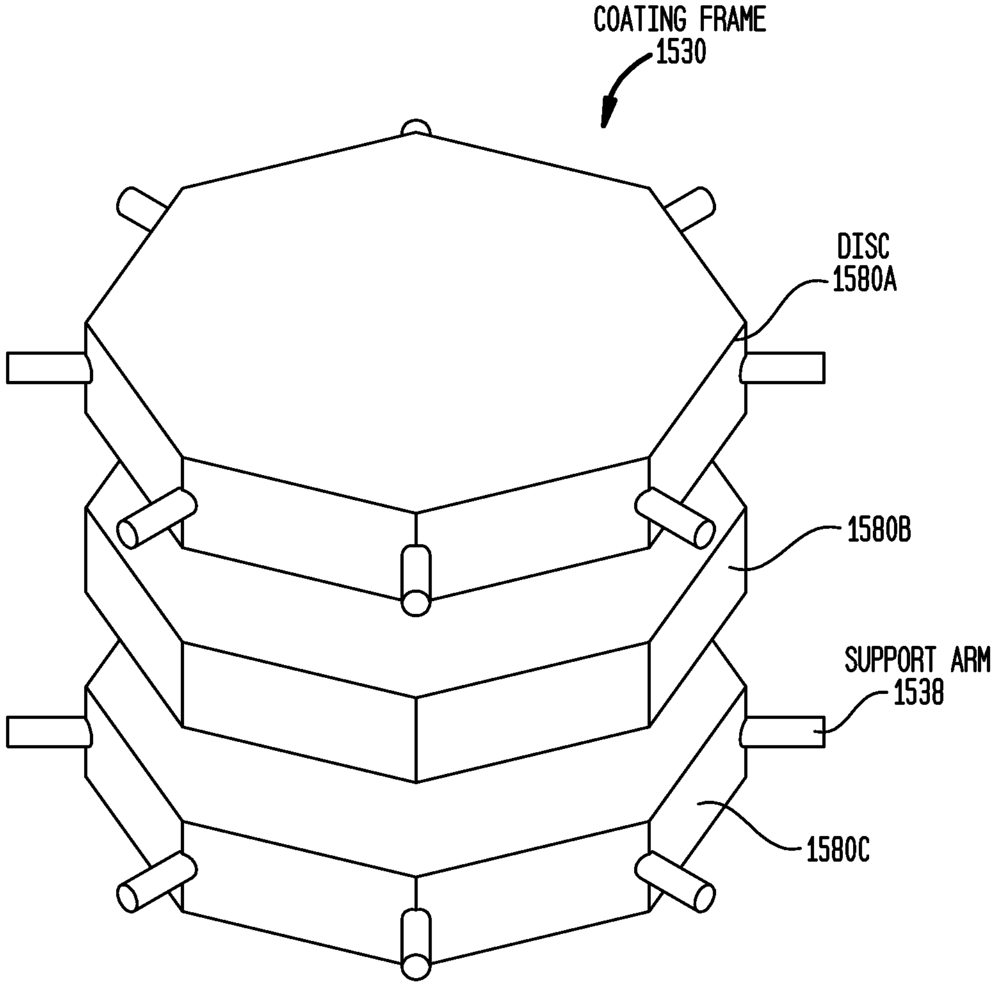
FIG. 15A is a perspective view of an alternative coating frame comprising a plurality of independently rotatable members.

FIG. 15A is a perspective view of an alternative coating frame 1530 that may used in embodiments of the present invention to coat an elongate conductive element with a substantially continuous barrier layer. As shown, coating frame 1530 comprises a plurality of independently rotatable discs 1580. Each disc 1580 comprises a plurality of support arms 1538 extending from the edge thereof.

In the illustrative embodiments of FIG. 15A, each of the discs 1580 are connected to one or more drive motors which mechanically rotate the discs. It would be appreciated that a variety of methods may be implemented to independently rotate discs 1580. It would also be appreciated that in certain embodiments discs 1580 may move side to side and/or forward and backwards, relative to a center axis extending through the discs. Such side to side and/or forward or backward movement may assist in minimize tension in the wire.

In the embodiments of FIG. 15A, a wire is loosely wound around discs 1580 so that the wire is supported by supports arms 1538, in substantially the same manner as described above with reference to FIGS. 9A and 9B. Coating frame 1530 is positioned in a deposition chamber so that a barrier layer may be applied to the wire. During deposition, one or more discs 1580 rotate, thereby altering the position of the wound wire to coating frame 1530. This ensures that no portion of the wound wire is in contact with a support arm 1538 for the entirety of the deposition, thereby providing a substantially continuous barrier layer on the wire.

Figure 15B:
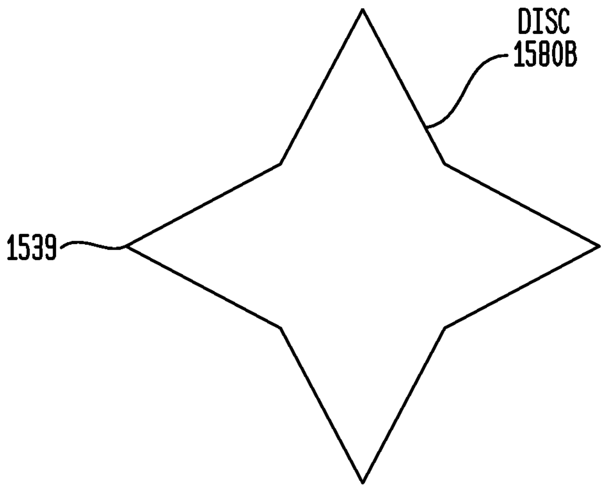
FIG. 15B is a top view of a rotatable member of in accordance with embodiments of the present invention.
Figure 15C:
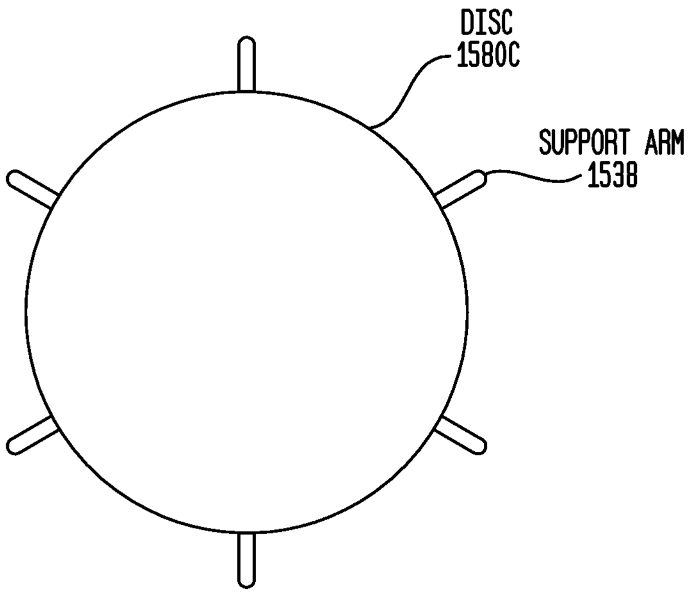
FIG. 15C is a top view of a rotatable member of in accordance with embodiments of the present invention.

FIG. 15A illustrates embodiments of the present invention in which discs 1538 have an octagonal cross-sectional shape and have support arms 1538 extending from the edges to support a wound wire. FIG. 15B illustrates an alternative embodiment in which a disc, referred to as disc 1580B, has a star shaped. In these embodiments, a wound wire would be supported near the points 1539 of disc 1580B. FIG. 15C illustrates a still other embodiment in which a disc 1580C as a circular cross-sectional shape, and support arms 1538 extend radially from the edge thereof. It would be appreciated that the shaped discs illustrated in FIGS. 15A-15C are merely illustrative and other shapes may also be implemented.

Figure 16:
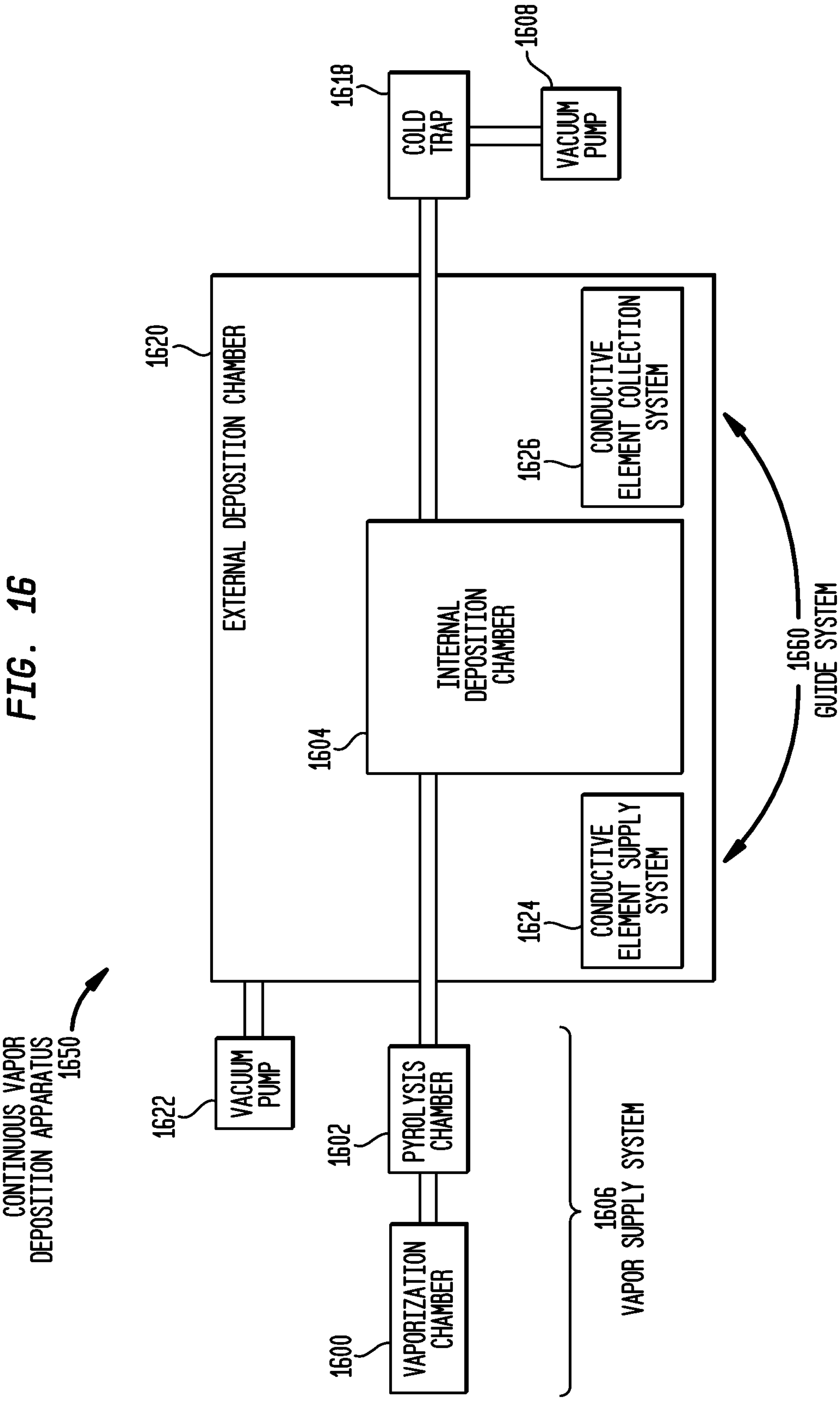
FIG. 16 is a schematic block diagram of a continuous vapor deposition apparatus, in accordance with embodiments of the present invention.

As noted above, embodiments of the present invention are generally directed to coating an elongate conductive element with a substantially continuous barrier layer. FIG. 16 is a schematic block diagram illustrating embodiments of a vapor deposition apparatus, referred to as continuous vapor deposition apparatus 1650, configured to apply a substantially continuous barrier layer to an elongate conductive element. As shown in FIG. 16, continuous vapor deposition apparatus 1650 comprises a vapor supply system 1606 configured to supply vapor material to an internal deposition chamber 1604. Vapor supply system 1606 includes a vaporization chamber 1600 that vaporizes a quantity of a dimer inserted therein, and a pyrolysis chamber 1602 connected to vaporization chamber 1600. Once transferred to pyrolysis chamber 1602, the vaporized dimer is pyrolized at temperatures of approximately 400 to 750 degrees Celsius to form a desired monomer vapor. Following pyrolysis, the monomer vapor is transferred to internal deposition chamber 1604, where, as described below, the vapor is used forms a substantially continuous barrier layer on the surface of a conductive element positioned in the chamber. In specific embodiments of the present invention, vapor deposition apparatus vaporizes a parylene dimer, and forms a parylene coating on a conductive element within internal deposition chamber 1604.

Following deposition and condensation, residual vapor is removed from deposition chamber 1604 and transferred to cold trap 1618. Cold trap 1618 serves to rapidly condense and polymerize any residual vapors. Vacuum pump 1608 is connected to cold trap 1618 and maintains continual negative pressure within internal deposition chamber 1604 and cold trap 1618.

As shown in FIG. 16, continuous vapor deposition apparatus 1650 further comprises a guide system 1660 positioned adjacent to internal deposition chamber 1604. As described in greater detail below, guide system 1660 is configured to apply a tensile force to a conductive element extending through internal deposition chamber 1604, and to control the movement of the conductive element through the internal deposition chamber during deposition. In the embodiment of FIG. 16, guide system 1660 comprises a conductive element supply system 1624 and a conductive element collection system 1626. As described in greater detail below, supply system 1624 is configured to guide a conductive element from a spool to the interior of internal deposition chamber 1604. Also as described below, collection system 1626 is configured to remove the conductive element from the internal deposition chamber 1604, and to spool the insulated conductive element exiting the internal deposition chamber.

As noted above, guide system 1660 is positioned adjacent to internal deposition chamber 1604. In the embodiments of FIG. 16, guide system 1660 is positioned within a sealed chamber, referred to herein as external deposition chamber 1620. External deposition 1620 provides a substantially contaminate free environment to house guide system 1660.

Furthermore, as shown in FIG. 16, external deposition chamber 1620 is connected to a vacuum pump 1622 that maintains negative pressure within the external chamber during operation. In certain embodiments, vacuum pumps 1608 and 1622 maintain the same pressure within internal and external deposition chambers 1604, 1620. In alternative embodiments, vacuum pumps 1608 and 1622 maintain different pressures with in internal and external deposition chambers 1604, 1620.

It would also be appreciated that in certain embodiments, vacuum may be removed from external deposition chamber 1620, while maintaining deposition vacuum pressure in internal deposition chamber 1604. In such embodiments, uncoated or coated spools of wire may be loaded into, or removed from, external deposition chamber 1604 without disturbing the deposition conditions (i.e. pressure and temperature) in internal deposition chamber.

Figure 17:
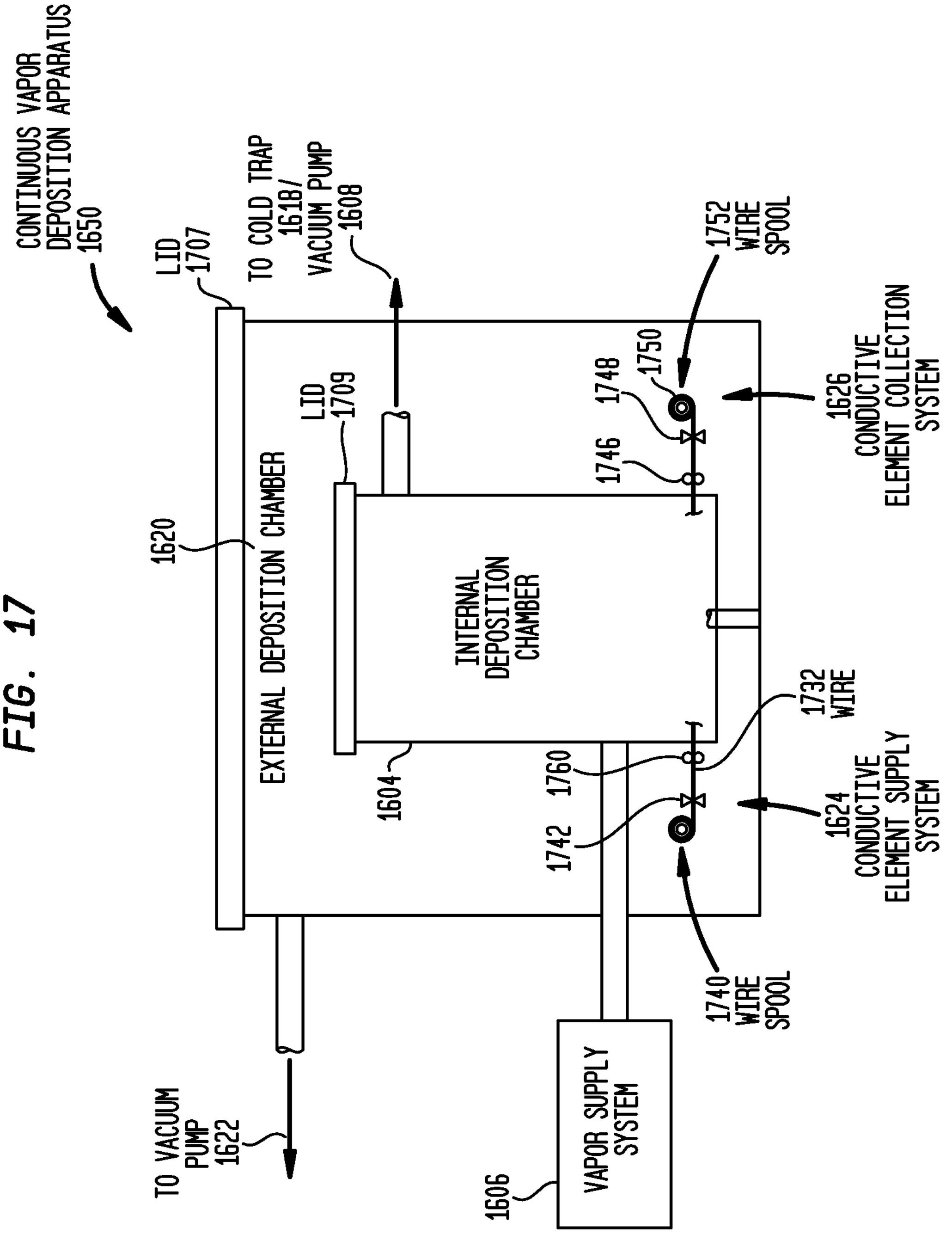
FIG. 17 is a schematic diagram illustrating further details of the continuous chemical deposition apparatus of FIG. 16, in accordance with embodiments of the present invention.

FIG. 17 is an additional schematic diagram of continuous vapor deposition apparatus 1650. As noted above, continuous vapor deposition apparatus 1650 includes a guide system 1660 to control movement of a wire 1732 through internal deposition chamber 1604. Also as noted, guide system 1660 a conductive element supply system 1624, and a conductive element collection system 1626. Supply system 1624 guides wire 1732 from spool 1740 to internal deposition chamber 1604. As described in detail with reference to FIG. 18A, wire 1732 extends through a measurement apparatus 1742 that measures the diameter of wire 1732, and around one or more wire guides 1760 before entering internal deposition chamber 1604.

Collection system 1626 guides wire 1732 from internal deposition chamber 1604 to a spool 1752. Specifically, upon exiting internal deposition chamber 1604, wire 1732 extends around one or more wire guides 1746, and through a second measurement apparatus 1748. Measurement apparatus 1748 is used to measure the thickness of the barrier layer on wire 1732. Coated wire 1732 is wound about spool 1752.

As noted above, in embodiments of the present invention, internal deposition chamber 1604 is positioned in an external deposition chamber 1620. In embodiments of the present invention, external deposition chamber 1620 comprises a lid 1707 that provides access to internal deposition chamber 1604. Similarly, internal deposition chamber 1604 comprises a lid 1709 which provides access of cleaning the chamber.

Figure 18A:
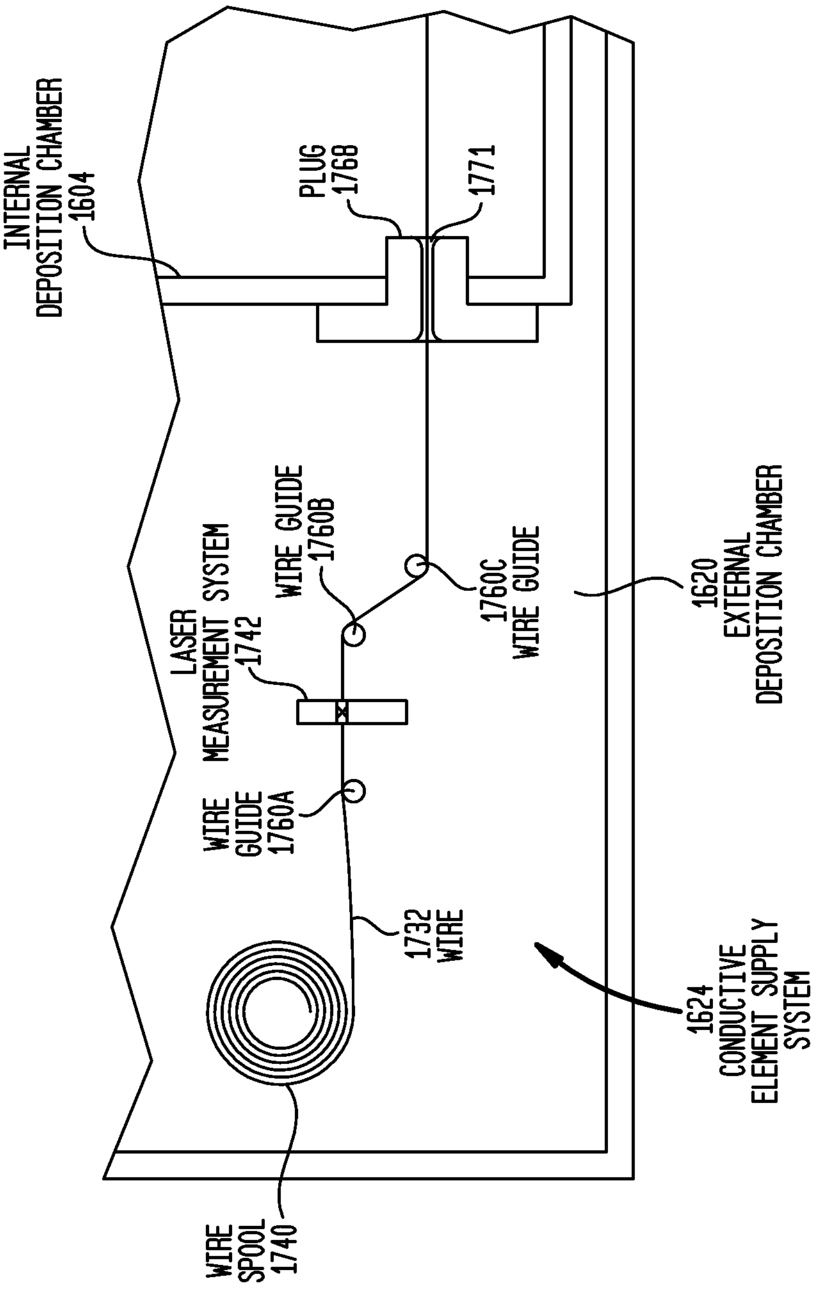
FIG. 18A is a detailed schematic diagram of one embodiment of the conductive element supply system of the continuous vapor deposition apparatus of FIG. 17.

FIG. 18A is a schematic diagram of one embodiment of conductive element supply system 1624. As noted, supply system 1624 comprises a spool 1740 of uncoated wire 1732. Wire 1732 extends from spool 1740 over a first wire guide 1760A through laser measurement system 1742. Laser measurement system 1742 determines the pre-coating thickness of wire 1732. As described below, this measured thickness is used during measurement of coating thickness by collection system 1626. Wire 1732 extends over and under, respectively, second and third wire guides 1760B and 1760C into internal deposition chamber 1604. It would be appreciated that a varying number of wire guides, locations and materials may be implemented in alternative embodiments of the present invention depending on, for example, the conductive element being coated.

Wire 1732 enters internal deposition chamber 1604 through an opening 1771 in a plug 1768. Opening 1771 in plug 1768 is of sufficient size to accommodate the passage of wire 1732 with little to no interference with the wire. For example, in one specific embodiment, opening 1771 has a 5 mm entrance diameter that tapers to 35 microns for a length of 10 mm, and expands to a diameter of 2 mm at the exit into internal deposition chamber 1604.

As described in greater detail below, the section of wire 1732 may follow a variety of travel paths through internal deposition chamber 1604. Wire 1732 exits through an opening 1773 in a plug 1769, shown in FIG. 18B. Plug 1769 and opening 1773 are substantially the same as plug 1769 and opening 1771, respectively, of FIG. 18A.

Figure 18B:
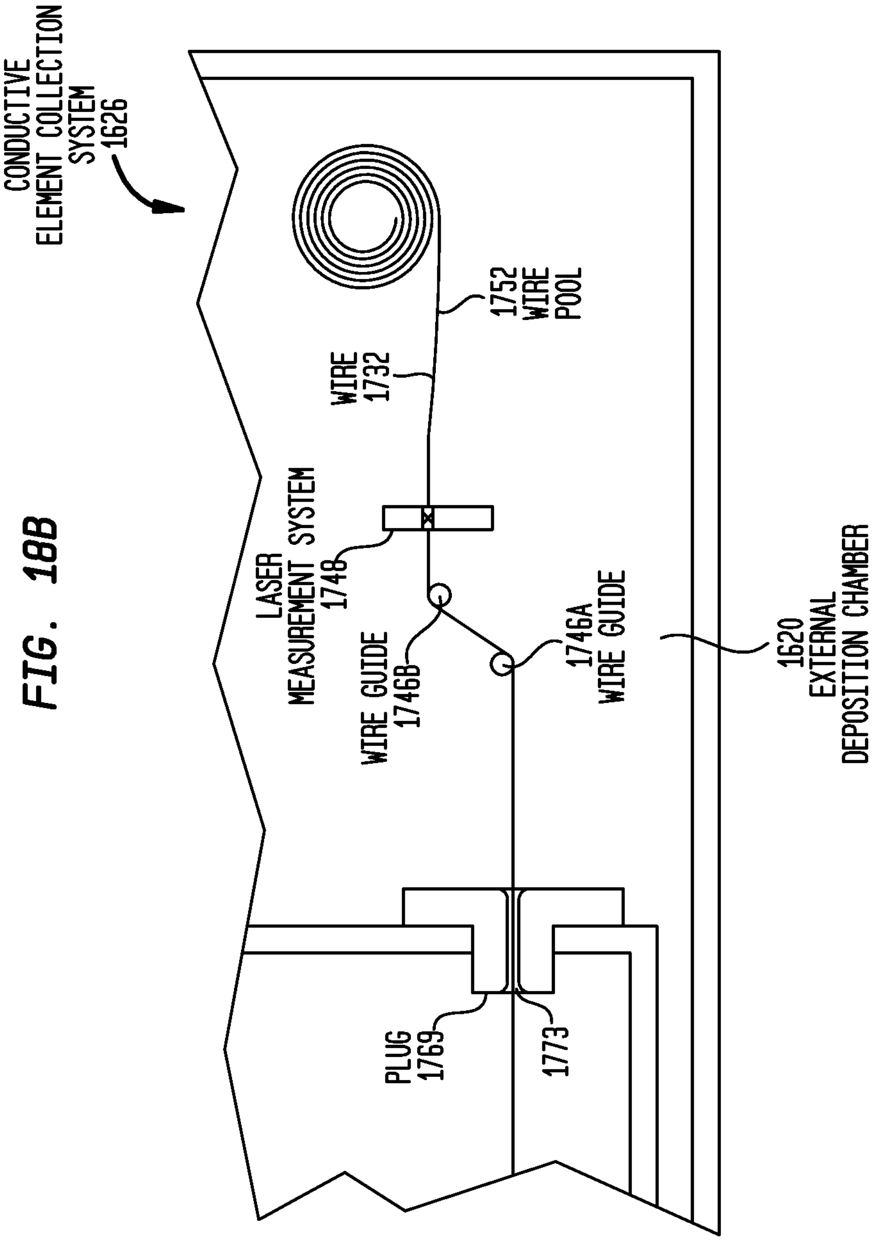
FIG. 18B is a detailed schematic diagram of one embodiment of the conductive element collection system of the continuous vapor deposition apparatus of FIG. 17.

FIG. 18B is a schematic diagram of conductive element collection system 1626. As shown, upon exiting opening 1773, coated wire 1732 extends under a first wire guide 1746A and over a second guide wire 1746B to laser measurement system 1748. Coated wire is then wound onto spool 1752. It would be appreciated that a varying number of wire guides, locations and materials may be implemented in alternative embodiments of the present invention depending on, for example, the conductive element being coated.

Laser measurement system 1748 is configured to measure the thickness of the barrier layer on wire 1732. In certain embodiments, laser measurement system 1748 measures the thickness using the data obtained by laser measurement system 1742 in supply system 1624.

In certain embodiments, laser measurement system 1742 may determine that the barrier layer does not have a sufficient thickness at one or more locations. In these circumstances, guide system 1660 is configured to reverse the direction of travel of wire 1732, and position those insufficiently coated sections of wire within internal deposition chamber 1604 for further deposition.

As noted, FIGS. 18A and 18B illustrate the details of supply system 1624 and collection system 1626. It would be appreciated that one or both of supply system 1624 and collection system 1626 function to control the tension on wire 1732. For example, in certain embodiments, collection system 1626 pulls wire 1732 through internal deposition chamber 1604, and supply system 1624 operates to release wire as necessary so that the desired tension is maintained.

Also as noted, in certain circumstances guide system 1660 is configured to reverse the direction of travel of wire 1732. In specific such embodiments, supply system 1624 pulls wire 1732 through internal deposition chamber 1604, and collection system 1626 operates to release wire as necessary so that the desired tension is maintained.

FIGS. 18A and 18B illustrate the use of plugs 1768 and 1769 through which wire 1732 passes to enter and exit, respectively, internal deposition chamber 1604. In embodiments of the present invention, plugs 1768, 1769 are removable to facilitate cleaning of internal deposition chamber 1604. In certain embodiments, plugs 1768, 1769 are formed from, for example, polytetrafluoroethylene (PTFE).

As noted above, wire 1732 may follow a variety of travel paths through internal deposition chamber 1604. FIGS. 19A-19D illustrate several different paths followed by wire 1732 in embodiments of the present invention. In certain such embodiments, wire 1732 is manually threaded from conductive element supply system 1624 through internal deposition chamber 1604 to conductive element supply system 1626. In other embodiments, guide system 1660 comprises a wire feed module which threads wire 1732 from spool 1740 to spool 1752.

Figure 19A:
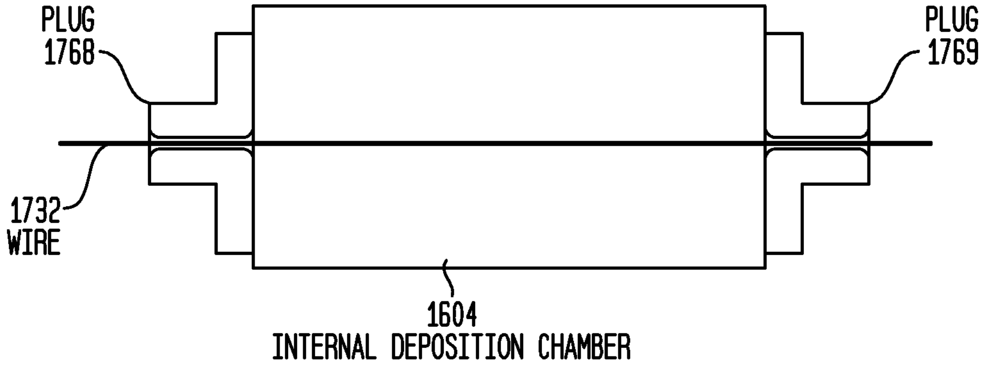
FIG. 19A is a cross-sectional view of an internal deposition chamber having a wire extending there through, in accordance with embodiments of the present invention.

FIG. 19A illustrates the simplest configuration in which wire 1732 enters through plug 1768, travels linearly through internal deposition chamber 1604, and exits through plug 1769. This illustrative configuration has the advantage of a simple travel path, and the need for few or no elements to support wire 1732 within the chamber. It would be appreciated that, in certain embodiments, the thickness of a deposited barrier layer may correspond to the length of time spent within internal deposition chamber 1604. The linear arrangement of FIG. 19A may alter the barrier layer thickness by conducting multiple passes through chamber 1604 with wire 1732. In alternative embodiments, internal deposition chamber 1604 may be designed to have a long length (eg. meters in length) through which wire 1732 extends.

Figure 19B:
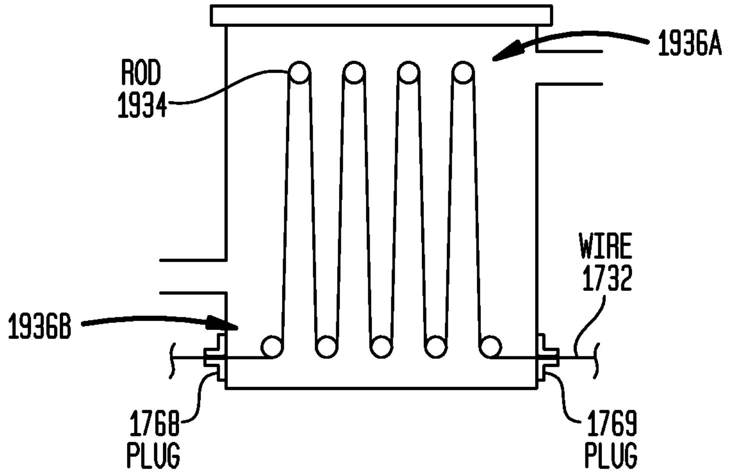
FIG. 19B is a cross-sectional view of an internal deposition chamber having a wire extending there through, in accordance with embodiments of the present invention.
Figure 19C:
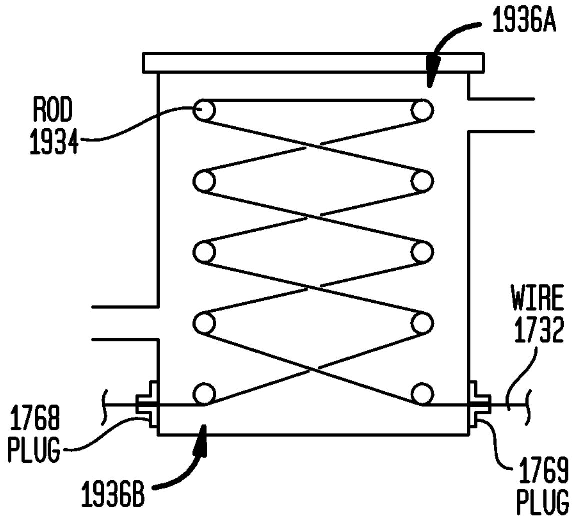
FIG. 19C is a cross-sectional view of an internal deposition chamber having a wire extending there through, in accordance with embodiments of the present invention.
Figure 19D:
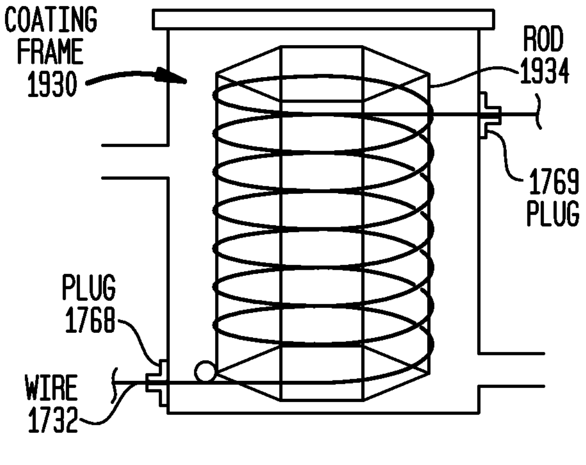
FIG. 19D is a cross-sectional view of an internal deposition chamber having a wire extending there through, in accordance with embodiments of the present invention.

FIG. 19B illustrates an alternative configuration in which several rods 1934 are provided within internal deposition chamber 1604. In these embodiments, rods 1934 are positioned in two horizontal, substantially parallel rows 1936. Wire 1732 enters internal deposition chamber 1604 through plug 1768 and is wound through the pattern of rods 1934. Wire 1732 exits through plug 1769. FIG. 19C illustrates embodiment similar to those of FIG. 19B in which rods 1934 are disposed in two vertical, substantially parallel rows 1938.

FIG. 19C illustrates another embodiment in which a coating frame 1930 that is substantially the same as the coating frame described above with reference to FIGS. 3A and 3B, is positioned in internal deposition chamber 1604. In these embodiments, wire 1732 is wound around rods 1934 in a helical pattern.

Figure 19E:
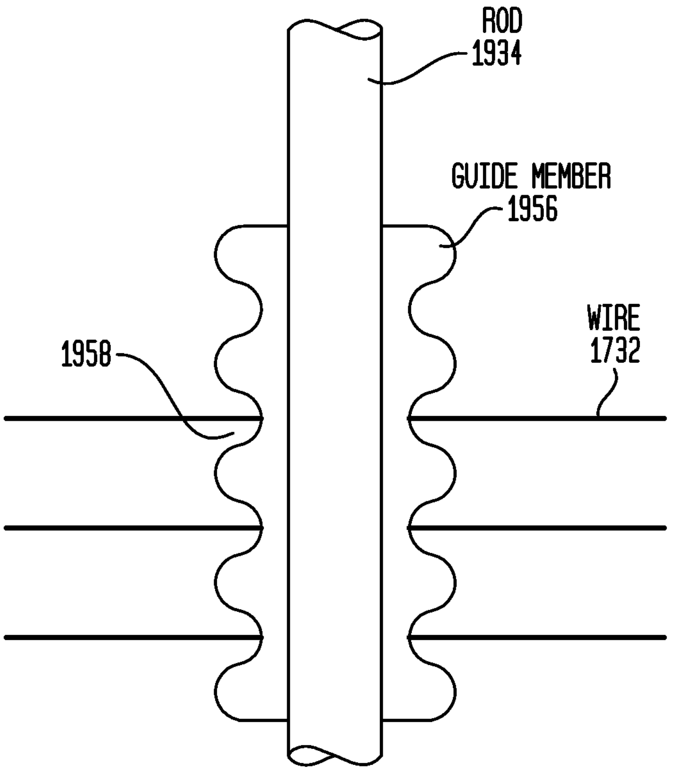
FIG. 19E is a side view of one embodiment of a rod and support arm used in embodiments of the continuous vapor deposition apparatus of FIG. 16.

In certain embodiments, wire 1732 may directly contact rods 1934 within internal deposition chamber 1604. In alternative embodiments, rods 1934 have one or more guide members 1956 that are configured to guide the wire through internal deposition chamber 1604. FIG. 19E illustrates one exemplary arrangement of a guide member 1956 comprising a plurality of notches 1958. In these embodiments, notches 1958 receive wire 1732 therein, and substantially prevent movement of the wire in directions other than the direction of travel.

As noted above, guide system 1660 is configured to move sections of wire 1732 through internal deposition chamber 1604. In certain embodiments of the present invention, wire 1732 remains stationary during deposition. In such embodiments, a coated section of wire may be removed from internal deposition chamber 1604, and an uncoated section may be simultaneously positioned in the chamber. Such movement may occur between sequential deposition processes.

In other embodiments, guide system 1660 is configured to continually move sections of wire 1732 through internal deposition chamber 1604 during a deposition process, sometimes referred to herein as deposition. In such embodiments, the barrier layer is provided on wire 1732 as it moves through internal deposition chamber 1604. Guide system 1660 is configured to move a section of wire 1732 at a speed that does not damage the wire, and which ensures that the section of conductive element is coated with a desired thickness of barrier material.

It would be appreciated that variations in the thickness of the barrier layer may be achieved by altering the time a section of wire 1732 remains within internal deposition chamber 1604. For example, in certain embodiments, the speed at which guide system 1660 moves a section of wire 1732 through internal deposition chamber 1604 may increased or decreased to alter the barrier layer thickness. Alternatively, as noted above, guide system 1660 is configured to reverse the direction of travel of wire 1732 so that a section may be moved forward as well as backwards to obtain a barrier layer of desired thickness.

Figure 20:
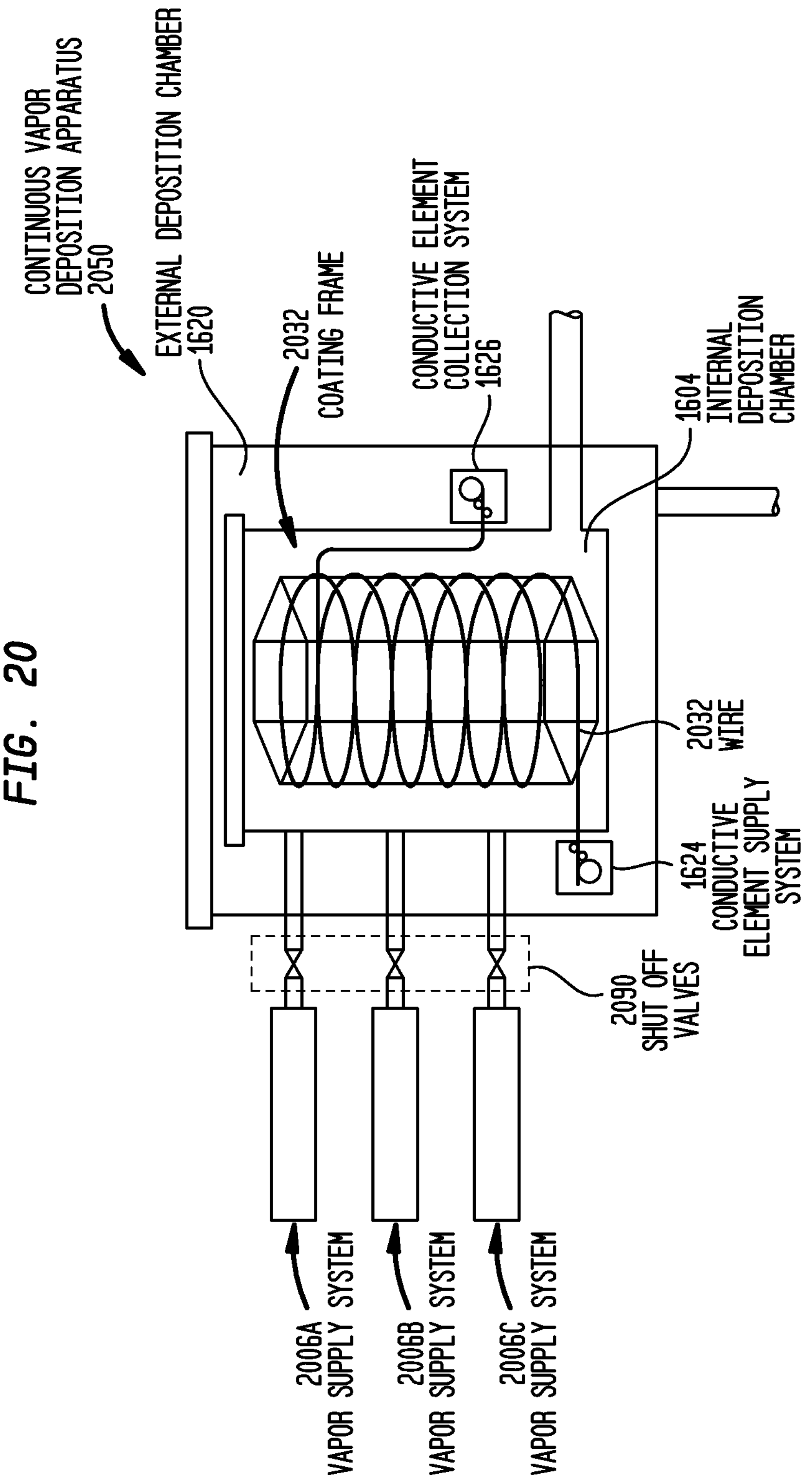
FIG. 20 is schematic view of further embodiments of a continuous vapor deposition apparatus, in accordance with embodiments of the present invention.

FIG. 20 is a schematic diagram illustrating an alternative continuous vapor deposition apparatus 2050 in accordance with embodiments of the present invention. Similar to the embodiments described above, continuous vapor deposition apparatus 2050 comprises an internal deposition chamber 1604, an external deposition chamber 1620, a conductive element supply system 1624 and a conductive element collection system 1626. Positioned in internal deposition chamber 1604 is a coating frame 2032 having wire 2032 wound there around.

Continuous vapor deposition apparatus 2050 further comprises a plurality of independently operable vapor supply systems 2006. Each vapor supply system 2006 is separately connected to internal deposition chamber 1604 so as to provide a vapor material to the chamber. A shut off valve 2090 is provided between each vapor supply system and internal deposition 1604 to control the flow of vapor into the chamber.

It would be appreciated that the operational time period for conventional vapor deposition apparatus is limited by the amount of material that is vaporized. This is a limitation because only a discrete amount of dimer may be loaded into the vaporization chamber at anytime. The embodiments of FIG. 20 increase the operational period for coating a conductive element because each vapor supply system 2006 may be independently operated. Therefore, one system may be loaded with dimer while the other is providing vapor. Thus, a continual supply of vapor may be provide to internal deposition chamber 1604, with only the non-operational time required to active an additional supply system.

The multiple vapor supply systems 2006 of FIG. 20 may be particularly beneficial in embodiments in which a section of wire is continually moved through internal deposition chamber 1604. By providing, through the use of multiple vapor supply systems 2006, a continuous flow of the vapor, the need to stop movement of wire 1732 through the chamber to add additional dimer is substantially eliminated. Thus, a wires ranging anywhere from several to hundreds of meters in length may be coated with a substantially continuous barrier layer.

Figure 21:
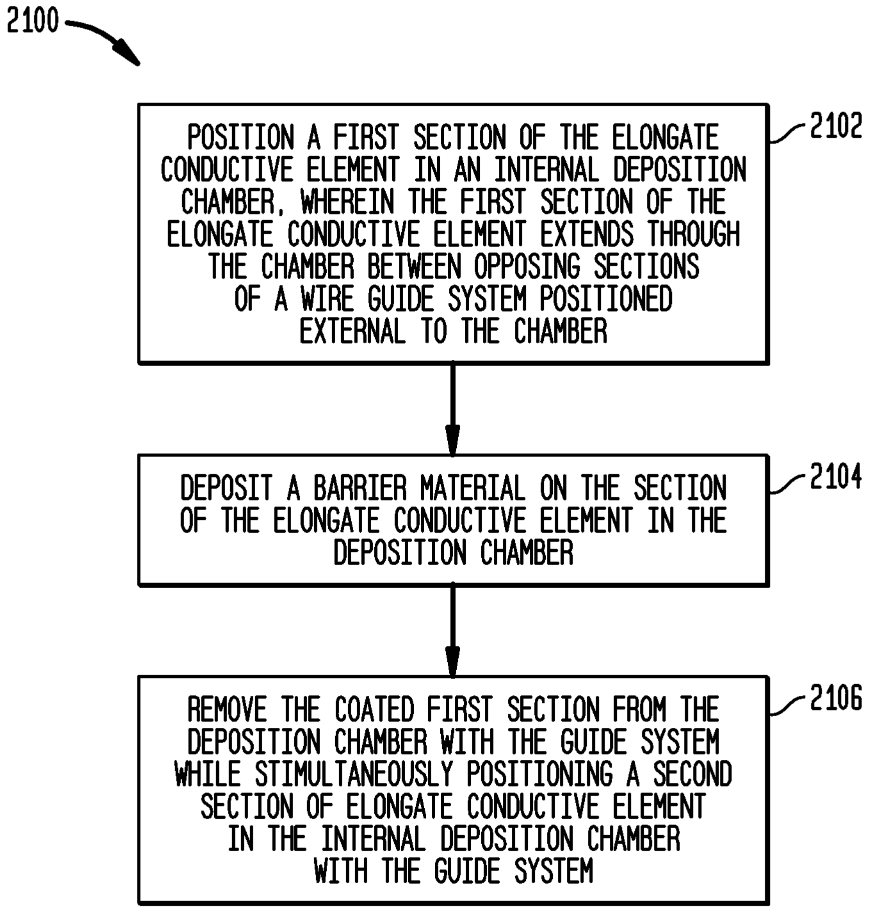
FIG. 21 is a flowchart illustrating the operations performed to form an elongate conductive element using a continuous vapor deposition apparatus in accordance with embodiments of the present invention.

FIG. 21 is a high level flowchart illustrating a method 2100 for coating an elongate, uncoated conductive element with a substantially continuous barrier layer using a continuous vapor deposition apparatus of the present invention. In such embodiments, the continuous vapor deposition apparatus comprises an internal deposition chamber.

The method begins at block 2102 in which a first section of the elongate conductive element is positioned in the internal deposition chamber. The first section of the elongate conductive element extends through the chamber between opposing sections of a guide system positioned external to the chamber. The method continues to block 2104 where a barrier material is deposited on the section of the elongate conductive element that is in the internal deposition chamber.

At block 2106, the coated first section is removed from the deposition chamber by the guide system. Simultaneously, the guide system positions a second section of elongate conductive element in the internal deposition chamber for deposition.

As noted above, in certain, a coated section of a conductive may be removed from an internal deposition chamber, and an uncoated section may be simultaneously positioned in the chamber between sequential deposition processes. In other embodiments, a conductive element may be continually moved through the internal deposition during deposition.

Figure 22A:
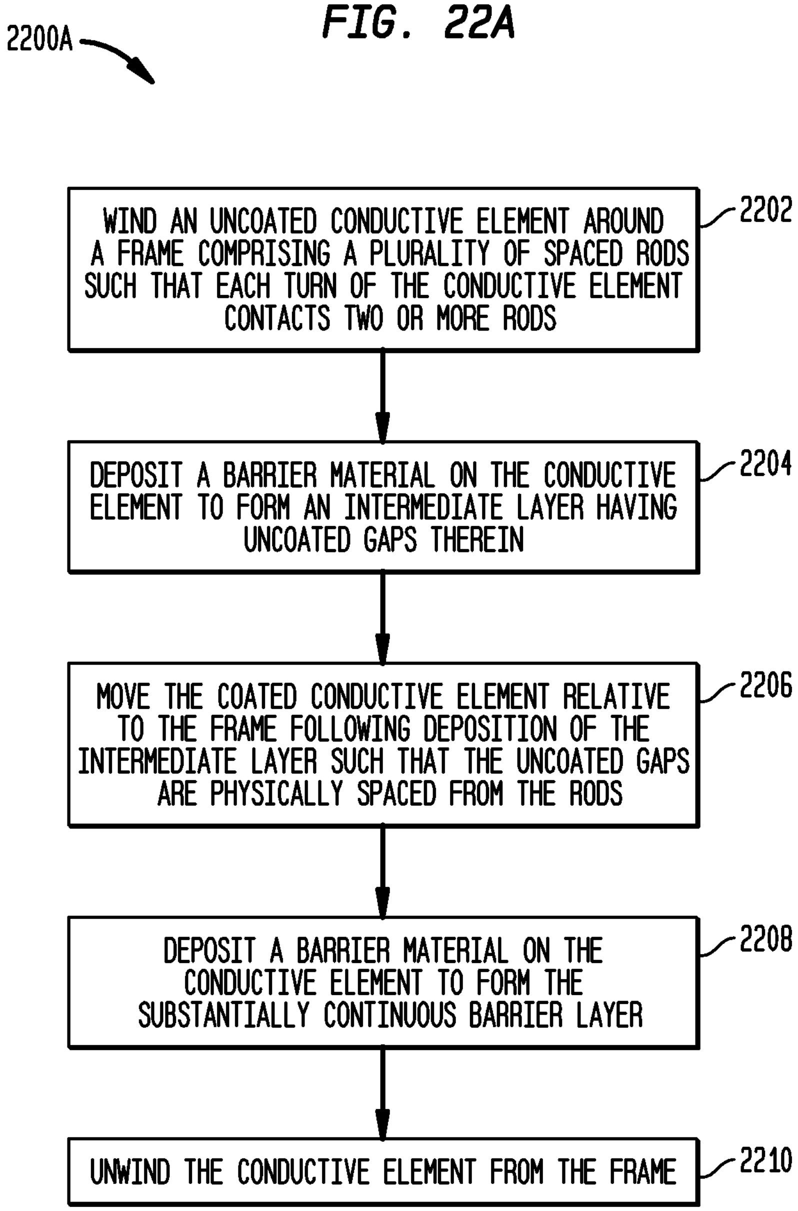
FIG. 22A is a flowchart illustrating the operations performed to form an elongate conductive element using movement of a wire with respect to a coating frame in accordance with embodiments of the present invention.
Figure 22B:
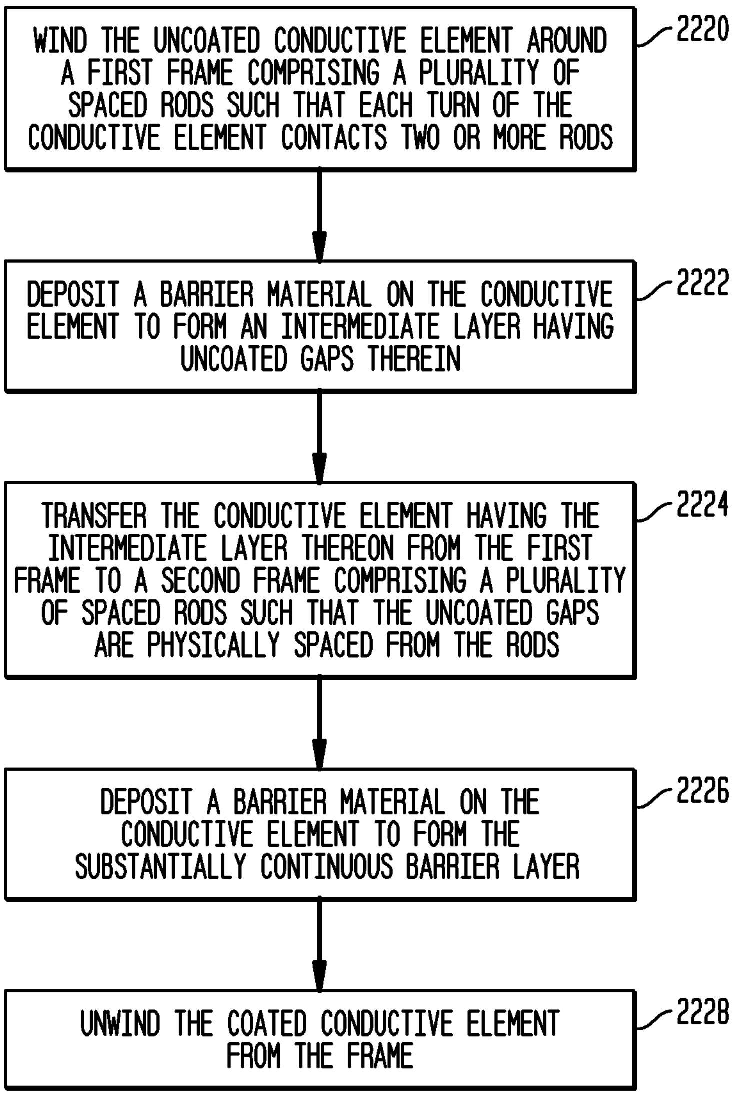
FIG. 22B is a flowchart illustrating the operations performed to form an elongate conductive element using movement of a wire from a first to a second coating frame in accordance with embodiments of the present invention.

As noted elsewhere herein, embodiments of the present invention are directed to coating an uncoated elongate conductive element with a substantially continuous barrier layer to form an insulated conductive element. Certain embodiments of the present invention described in detail below are directed to forming the substantially continuous barrier layer through relative movement of a wire to a coating frame between sequential coatings of a barrier material. FIGS. 22A and 22B illustrate two exemplary such embodiments.

Figure 23A:
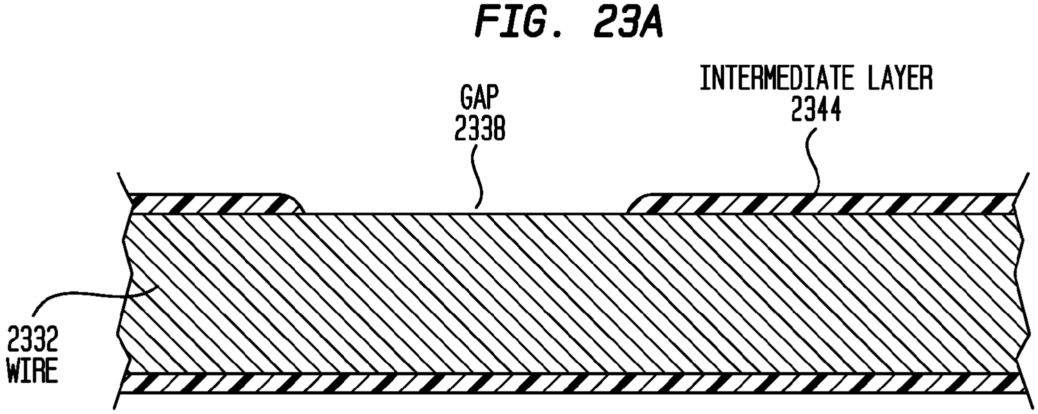
FIG. 23A is a cross-sectional view of a wire coated with an intermediate layer in accordance with embodiments of the present invention.

FIG. 22A is flowchart illustrating a method 2200A for coating an elongate, uncoated conductive element with a substantially continuous barrier layer, through motion of a wire relative to a coating frame between sequential coatings Method 2200A begins at block 2202 in which uncoated conductive element is wound around a plurality of spaced rods. The method continues at block 2204 in which a barrier material is deposited on the conductive element to form an intermediate layer having uncoated gaps therein. FIG. 23A illustrates an exemplary conductive element, shown as wire 2332, having an intermediate layer 2344 thereon. Intermediate layer 2344 has gaps 2338 therein. It would be appreciated that the thickness of layer 2344 relative to the size of gap 2338 shown in FIG. 23A is not shown to scale, and is merely illustrative.

At block 2206, following deposition of the intermediate layer on the conductive element, the coated conductive element is moved relative to the coating frame such that the uncoated gaps are physically spaces from the rods. In other words, the conductive element is moved relative to the frame so that the gaps are exposed and may receive a coating of barrier material. At block 2208, a barrier material is deposited on the coated conductive element. This coating of barrier material is referred to herein as a secondary layer. As noted, because the gaps in the intermediate layer are exposed, and are not in direct contact with the supports, the gaps receive a coating of the secondary layer to form a substantially continuous barrier layer. At block 2210, the insulated conductive element is unwound from the coating frame.

Figure 23B:
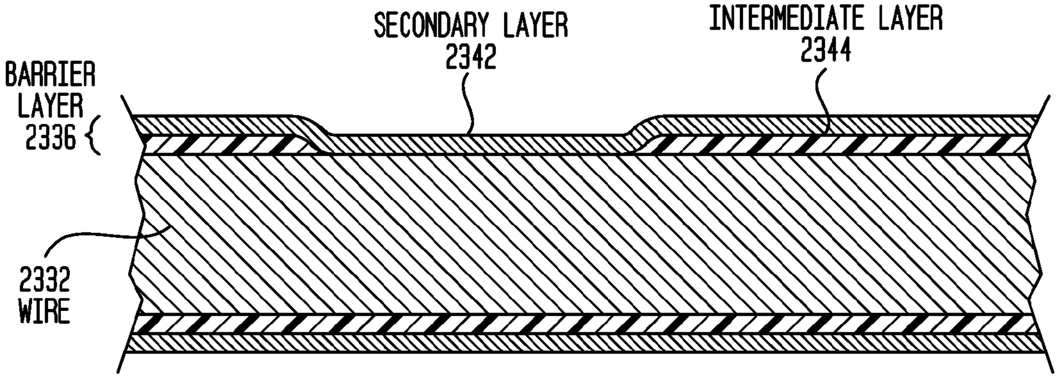
FIG. 23B is a side view of coated wire coated with a barrier layer in accordance with embodiments of the present invention.

FIG. 23B illustrates an insulated conductive element comprising a barrier layer 2336 formed from an intermediate layer 2344 and a secondary layer 2342. For ease of illustration, secondary layer 2342 and intermediate layer 2344 have been shown using different cross-hatching. It would be appreciated that layers 2342 and 2344 may comprise the same or different barrier material. In certain embodiments, both intermediate layer 2344 and secondary later 2342 each comprise layers of parylene.

FIG. 22A illustrates embodiments of the present invention in which the conductive element receives two coatings of a barrier material. It would be appreciated that each of the coatings may have the same or different thickness. It would also be appreciated that in certain embodiments additional coatings may be applied.

FIG. 22B illustrates an alternative embodiments of the present invention in which a substantially continuous barrier layer is formed by transferring a conductive element from a first coating frame to a second coating frame between sequential coatings of a barrier material. Method 2200B of FIG. 22B begins at block 2220 in which an uncoated conductive element is wound around a coating frame comprising a plurality of spaced rods. The method continues at block 2222 where a barrier material is deposited on the conductive element to form an intermediate layer having uncoated gaps therein. As noted above, FIG. 23A illustrates an exemplary conductive element, shown as wire 2332, having an intermediate layer 2344 thereon. Intermediate layer 2344 has gaps 2338 therein.

At block 2224, the conductive element having the intermediate layer thereon is transferred from the first coating frame to a second coating frame comprising a plurality of spaced rods. The coated conductive element is wound around the second coating frame such that the uncoated gaps in the intermediate layer are physically spaced from the rods. In other words, the conductive element is wound around the second frame so that the gaps are exposed and may receive a coating of barrier material.

At block 2226, a barrier material is deposited on the coated conductive element. This coating of barrier material is referred to herein as a secondary layer. Because, as noted, the coated conductive element is wound around the second coating frame such that the gaps in the intermediate layer are exposed, the gaps receive a coating of the secondary layer to form a substantially continuous barrier layer. At block 2228, the insulated conductive element is unwound from the second coating frame.

As noted above, FIG. 23B illustrates an insulated conductive element comprising a barrier layer 2336 formed from an intermediate layer 2344 and a secondary layer 2342. For ease of illustration, secondary layer 2342 and intermediate layer 2344 have been shown using different cross-hatching. It would be appreciated that layers 2342 and 2344 may comprise the same or different barrier material. In certain embodiments, both intermediate layer 2344 and secondary later 2342 comprise layers of parylene.

Figure 24A:
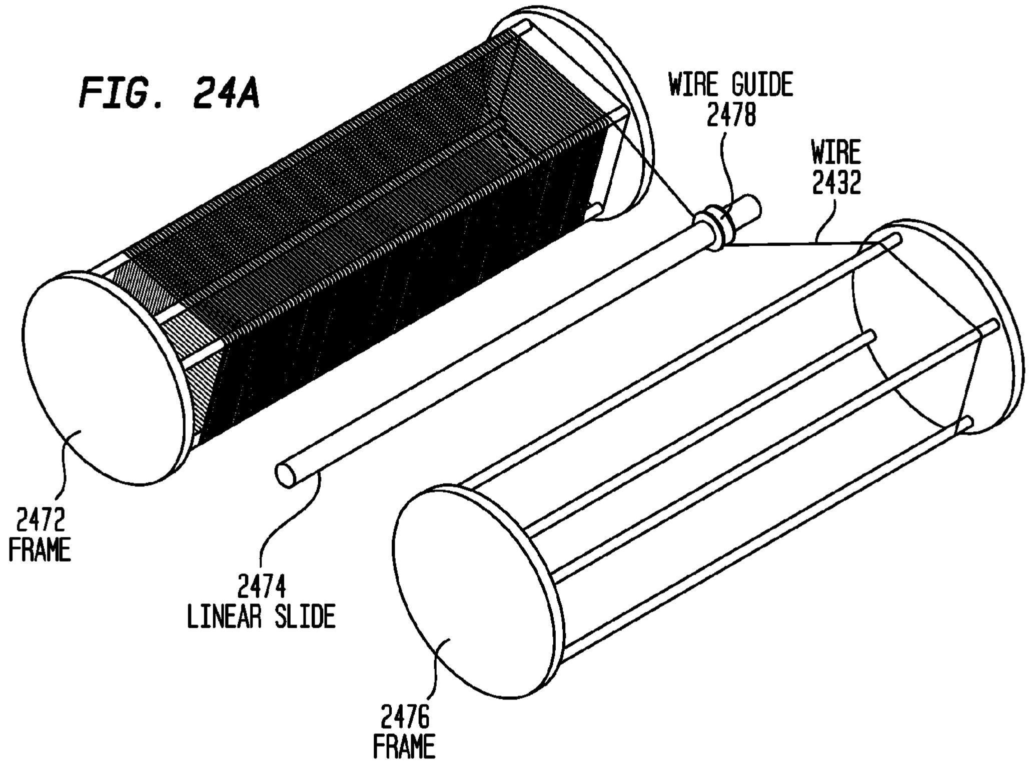
FIG. 24A is a perspective view of a wire guide system for transferring a partially coated wire from a first coating frame to a second coating frame.

As noted above, FIG. 22B illustrates embodiments of the present invention in which a coated conductive element is transferred from a first coating frame to a second coating frame between coats of a barrier material. FIG. 24A is a schematic diagram illustrating one exemplary mechanism for transferring a coated wire 2432 from a first coating frame 2472 to a second coating frame 2476. In these embodiments, the transfer mechanism comprises a linear slide 2476 and a wire guide 2478. As wire 2432 is wound from coating frame 2472, the wire passes through wire guide 2478 to coating frame 2476. Wire guide 2478 moves along slide 2474 to control the location of wire 2432 as it is wound around coating frame 2476.

Figure 24B:
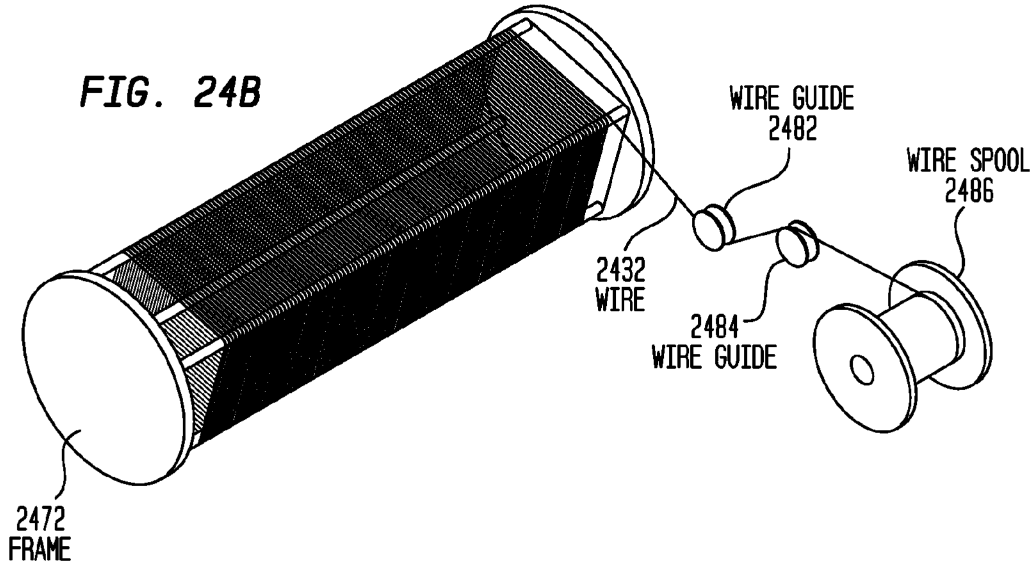
FIG. 24B is a perspective view of a wire guide system for transferring a partially coated wire from a first coating frame to a second coating frame.

FIG. 24B illustrates embodiments of the present invention for transferring a coated wire 2432 from a coating frame 2472 to a wire spool 2486. In these embodiments, the transfer mechanism comprises first and second wire guides 2482 and 2484. As wire 2432 is wound from coating frame 2472, the wire passes through wire guide 2482 to wire 2484 which aligns the wire with spool 2486.

As noted above, embodiments of the present invention are generally directed to using vapor deposition to coat elongate conductive elements with a protective barrier layer. The barrier layer may be applied to the conductive elements for a variety of reasons including, but not limited to providing electrical insulation between adjacent conductive elements, providing biocompatibility, immobilization of microscopic particles, and ensuring that the conductive elements are passive, as well as providing physical isolation of the conductive elements from moisture, chemicals, and other substances.

In certain embodiments, the barrier layer utilized in embodiments of the present invention is a polymeric material. In one particular embodiment, the barrier layer is parylene. Parylene is the generic name for a variety of vapor deposited poly-para-xylylenes. These materials form highly-crystalline polymers that may be applied as conformal coatings and films. Parylene, unlike other polymeric materials, is not manufactured or sold as a polymer. Rather it is produced by vapor-phase deposition and polymerization of para-xylylene or its derivatives.

There are a variety of derivatives and isomers of parylene. The most common variants include Parylene C, Parylene N, and Parylene D. It would be appreciated that other variants of parylene are also commercially available. It would be appreciated that substantially any variant of parylene may be used in embodiments of the present invention.

It would also be appreciated that alternative barrier materials may be utilized in embodiments of the present invention. Exemplary alternative barrier materials include, but are not limited to, Polysilicon, Silicon dioxide and Silicone nitride.

As noted elsewhere herein, coating frames, rods, support arms etc., described above may be formed from any biocompatible material which has sufficient strength to maintain a desired shaped. In specific embodiments, a coating frame, rod, support arm, etc. may be formed from stainless steel. In certain embodiments, a coating frame, rod, support arm, etc. may be coated with, for example, PTFE to reduce the bonding between the barrier material and a coating frame, rod, support arm, etc.

Embodiments of the present invention have been described herein with reference to an elongate conductive element having a substantially continuous barrier layer, or substantially continuous sections. It would be appreciated that the thickness of a substantially continuously coated section or layer need not be consistent across the entire section or layer.

As noted above, insulated conductive elements in accordance with embodiments of the present invention may be implemented in an implantable stimulating assembly. Such a stimulating assembly may be used for a variety of cochlear implants, such as short stimulating assemblies, straight stimulating assemblies, peri-modiolar stimulating assemblies, etc. Insulated conductive elements in accordance embodiments of the present invention may also be implemented in any implantable medical device utilizing coated conductive elements. For example, embodiments of the present invention may be implemented in any neurostimulator now know or later developed, such as brain stimulators, cardiac pacemakers/defibrillators, functional electrical stimulators (FES), spinal cord stimulators (SCS), bladder stimulators, etc.

Further features and advantages of the present invention are described in commonly owned and co-pending U.S. Utility patent applications entitled "An Insulated Conductive Element Comprising Substantially Continuously Coated Sections Separated By Uncoated Gaps," filed Sep. 9, 2009; "An Insulated Conductive Element Comprising Substantially Continuous Barrier Layer Formed Through Multiple Coatings," filed Sep. 9, 2009; and "An Insulated Conductive Element Having A Substantially Continuous Barrier Layer Formed Through Continuous Vapor Deposition," filed Sep. 9, 2009. The content of these applications are hereby incorporated by reference herein.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method of coating an elongate, uncoated conductive element with a substantially continuous barrier layer, comprising:

winding the uncoated conductive element around a frame comprising spaced supports such that sections of the conductive element are positioned in contact with two or more supports;

depositing a barrier material on the conductive element to form the barrier layer;

adjusting the relative position of the conductive element to the frame during deposition such that the sections of the conductive element are physically separated from the supports for a time that is sufficient to form a substantially continuous barrier layer on the conductive element; and unwinding the coated conductive element from the frame.

2. The method of claim 1, wherein adjusting the relative position of the conductive element to the frame during deposition comprises:

vibrating the frame during deposition.

3. The method of claim 2, wherein the frame is connected to a frame drive system comprising a motor configured to rotate the frame and an offset cam, and wherein the method further comprises:

generating vibration of frame with the offset cam during rotation of the frame by the motor.

4. The method of claim 2, wherein the frame is connected to a spring, and wherein the method further comprises:

generating vibration of the frame with the spring during deposition.

5. The method of claim 1, wherein the spaced supports comprise a plurality of substantially parallel rods, and wherein winding the uncoated conductive element comprises:

helically winding the uncoated conductive element around the plurality of rods such that each turn of the wound conductive element contacts each of the rods.

6. The method of claim 5, wherein the plurality of rods are configured to be positioned substantially horizontal in a deposition chamber to collectively rotate about a substantially horizontal axis during deposition, and wherein winding the uncoated conductive element around the plurality of rods further comprises:

winding the conductive element under a tension that substantially prevents the movement of the conductive element during rotation of the plurality of rods.

7. The method of claim 5, wherein the plurality of rods are configured to be positioned substantially horizontal in a deposition chamber to collectively rotate about a substantially horizontal axis during deposition, and wherein winding the uncoated conductive element around the plurality of rods further comprises:

loosely winding the conductive element around the rods such that conductive element becomes spaced from each rod during rotation of the plurality of rods.

8. The method of claim 6, wherein opposing ends of each of the plurality of rods of disposed in guides, and wherein the method further comprising:

rotating the frame during deposition such that the opposing ends at least one of rotate and move linearly within the guides.

9. The method of claim 1, wherein the spaced supports comprise a plurality of support arms extending from substantially parallel rods, and wherein winding the uncoated conductive element around the frame comprises:

loosely winding the conductive element around the frame such that conductive element follows a helical path about the rods, and such that the conductive element is positioned only on the support arms.

10. The method of claim 1, wherein the frame comprises a tubular structure and wherein the spaced support members comprise one or more notches in the surface of the tubular structure, and wherein winding the conductive element around the frame comprises:

loosely winding the conductive element around the frame such that conductive element follows a helical path about the tubular member through the notches.

11. The method of claim 1, wherein the frame comprises a plurality of independently rotatable disks, and wherein the spaced supports comprise a plurality of support arms extending from disks, and wherein the method further comprises:

rotating the risks with respect to one another to adjust the position of the conductive element to the support arms.

12. The method of claim 1, wherein the barrier material is deposited on the conductive element within a deposition chamber, wherein adjusting the relative position of the conductive element to the frame during deposition comprises:

continually moving the conductive element through the deposition chamber during deposition.

13. The method of claim 12, and wherein continually moving the conductive element during deposition further comprises:

moving the conductive element such that a section of conductive element enters and exits the deposition chamber in a time period that is sufficient to form a desired thickness of barrier material on the section of conductive element.

14. The method of claim 1, wherein adjusting the relative position of the conductive element to the frame during deposition comprises:

periodically moving the conductive element during deposition.

15. The method of claim 1, wherein depositing a barrier layer on the conductive element comprises:

depositing at least one layer of parylene on the conductive element.

16. A method of coating an elongate, uncoated conductive element, comprising:

winding the uncoated conductive element around a frame comprising spaced supports such that sections of the conductive element are positioned in contact with the supports;

depositing a barrier material on the conductive element;

moving at least one of the conductive element and the frame relative to one another during deposition of the barrier material such that a substantially continuous barrier layer is formed on the surface of the conductive element; and unwinding the coated conductive element from the frame.

17. The method of claim 16, wherein moving at least one of the conductive element and the frame relative to one another during deposition comprises:

vibrating the frame during deposition.

18. The method of claim 17, wherein the frame is connected to a frame drive system comprising a motor configured to rotate the frame and an offset cam, and wherein the method further comprises:

generating vibration of frame with the offset cam during rotation of the frame by the motor.

19. The method of claim 17, wherein the frame is connected to a spring, and wherein the method further comprises:

generating vibration of the frame with the spring during deposition.

20. The method of claim 16, wherein the spaced supports comprise a plurality of substantially parallel rods, and wherein winding the uncoated conductive element comprises:

helically winding the uncoated conductive element around the plurality of rods such that each turn of the wound conductive element contacts each of the rods.

21. The method of claim 20, wherein the plurality of rods are configured to be positioned substantially horizontal in a deposition chamber to collectively rotate about a substantially horizontal axis during deposition, and wherein winding the uncoated conductive element around the plurality of rods further comprises:

winding the conductive element under a tension that substantially prevents the movement of the conductive element during rotation of the plurality of rods.

22. The method of claim 20, wherein the plurality of rods are configured to be positioned substantially horizontal in a deposition chamber to collectively rotate about a substantially horizontal axis during deposition, and wherein winding the uncoated conductive element around the plurality of rods further comprises:

loosely winding the conductive element around the rods such that conductive element becomes spaced from each rod during rotation of the plurality of rods.

23. The method of claim 21, wherein ends of each of the plurality of rods of disposed in guides, and wherein the method further comprising:

rotating the frame during deposition such that the opposing ends at least one of rotate and move linearly within the guides.

24. The method of claim 16, wherein the spaced supports comprise a plurality of support arms extending from substantially parallel rods, and wherein winding the uncoated conductive element around the frame comprises:

loosely winding the conductive element around the frame such that conductive element follows a helical path about the rods, and such that the conductive element is positioned only on the support arms.

25. The method of claim 16, wherein the frame comprises a tubular structure and wherein the spaced support members comprise one or more notches in the surface of the tubular structure, and wherein winding the conductive element around the frame comprises:

loosely winding the conductive element around the frame such that conductive element follows a helical path about the tubular member through the notches.

26. The method of claim 16, wherein the frame comprises a plurality of independently rotatable disks, and wherein the spaced supports comprise a plurality of support arms extending from disks, and wherein the method further comprises:

rotating the risks with respect to one another to adjust the position of the conductive element to the support arms.

27. The method of claim 16, wherein the barrier material is deposited on the conductive element within a deposition chamber, wherein adjusting the relative position of the conductive element to the frame during deposition comprises:

continually moving the conductive element through the deposition chamber during deposition.

28. The method of claim 27, and wherein continually moving the conductive element during deposition further comprises:

moving the conductive element such that a section of conductive element enters and exits the deposition chamber in a time period that is sufficient to form a desired thickness of barrier material on the section of conductive element.

29. The method of claim 16, wherein adjusting the relative position of the conductive element to the frame during deposition comprises:

periodically moving the conductive element during deposition.

30. The method of claim 16, wherein depositing a barrier layer on the conductive element comprises:

depositing at least one layer of parylene on the conductive element.

31. The method of claim 16, wherein the method further comprises:

winding the insulated conductive element onto a spool, wherein the spooled length of the insulated conductive element is approximately equal to the length of the uncoated conductive element wound around the frame.

32. The method of claim 16, wherein depositing a barrier layer on the conductive element comprises:

depositing at least one layer of parylene on the conductive element.

33. A method of coating an elongate, uncoated conductive element with a substantially continuous barrier layer, comprising:

positioning the uncoated conductive element proximate a support apparatus comprising spaced supports such that sections of the conductive element are supported by the spaced supports; and depositing a barrier material on the conductive element to form the barrier layer, wherein during the action of depositing the barrier, the relative position of the conductive element to the support apparatus is adjusted such that a substantially continuous barrier layer on the conductive element is formed.

34. The method of claim 33, wherein the adjustment of the relative position of the conductive element to the support apparatus during the action of depositing the barrier includes physically separating the sections of the conductive element from the supports.

* * * * *